(12) United States Patent
Kopito et al.

(10) Patent No.: US 7,790,364 B2
(45) Date of Patent: Sep. 7, 2010

(54) COMPOSITIONS AND METHODS FOR HIGH THROUGHPUT SCREENING OF PHARMACOLOGICAL CHAPERONES

(75) Inventors: Ron R. Kopito, Stanford, CA (US); Wei Zhang, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 472 days.

(21) Appl. No.: 11/698,513

(22) Filed: Jan. 26, 2007

(65) Prior Publication Data

US 2007/0270486 A1 Nov. 22, 2007

Related U.S. Application Data

(60) Provisional application No. 60/762,674, filed on Jan. 27, 2006.

(51) Int. Cl.
*C12Q 1/00* (2006.01)
*C12Q 1/25* (2006.01)
*G01N 33/53* (2006.01)
*G01N 33/533* (2006.01)
*G01N 33/535* (2006.01)
*G01N 33/577* (2006.01)
*G01N 33/566* (2006.01)

(52) U.S. Cl. ............... 435/4; 435/7.2; 435/7.21; 435/174; 435/7.1; 435/332

(58) Field of Classification Search ............... None
See application file for complete search history.

(56) References Cited

U.S. PATENT DOCUMENTS 5,057,412 A 10/1991 Rabin
5,888,722 A 3/1999 Costa De Beauregard
6,451,541 B1 9/2002 Winnacker
2003/0236298 A1 12/2003 Meng
2005/0019773 A1 1/2005 McAlister

OTHER PUBLICATIONS

Schultz et al., Am J Physiol. 1997; 273: C2080-9.*
Hackbarth et al., Biotechniques. 2004; 37: 835-9.*
Backer et al., "Engineering S-protein fragments of bovine ribonuclease A for targeted drug delivery", Protein Expr. Purif., 2002, 26(3):455-461.
Beintema et al., "Molecular evolution of pancreatic-type ribonucleases", Mol. Biol. Evol., 1986, 3(3):262-275.
Bertrand et al., "The role of regulated CFTR trafficking in epithelia secretion", Am. J. Physiol. Cell Physiol., 2003, 285: C1-C18.
Dwyer et al., "High affinity RNase S-peptide variants obtained by phage display have a novel "hot-spot" of binding energy", Biochemistry, 2001, 40(45):13491-500.
Gelman et al., "Rescuing protein conformation: prospects for pharmacological therapy in cystic fibrosis", J. Clin. Invest., 2002, 110:1591-1597.
James and Woolley, "A fluorescence-based assay for ribonuclease A activity", Anal. Biochem., 1998, 264:26-33.
Park et al., "Fast, facile, hypersensitive assays for ribonucleolytic activity", Methods Enzymol., 2001, 341:81-94.

* cited by examiner

*Primary Examiner*—Bridget E Bunner
*Assistant Examiner*—Christina Borgeest
(74) *Attorney, Agent, or Firm*—Bozicevic, Field & Francis LLP; Pamela J. Sherwood

(57) ABSTRACT

Assays are provided for the screening and classification of biologically active agents that alter the conformation of conformationally defective proteins. The methods of the invention find use in the identification and classification of agents with chaperone activity, particularly the identification and classification of small molecule chemical and pharmacological chaperones. The agents thus identified find use altering the conformation of otherwise conformationally defective proteins.

7 Claims, 11 Drawing Sheets

(2 of 11 Drawing Sheet(s) Filed in Color)

SEQUENCE LISTING

```
<160> NUMBER OF SEQ ID NOS: 41

<210> SEQ ID NO 1
<211> LENGTH: 19
<212> TYPE: PRT
<213> ORGANISM: bovine

<400> SEQUENCE: 1

Lys Glu Thr Ala Ala Ala Lys Phe Glu Arg Gln His Met Asp Ser Ser
1               5                   10                  15

Thr Ser Ala

<210> SEQ ID NO 2
<211> LENGTH: 19
<212> TYPE: PRT
<213> ORGANISM: Artificial Sequence
<220> FEATURE:
<223> OTHER INFORMATION: synthetic S-tags

<400> SEQUENCE: 2

Lys Glu Thr Asn Trp Ala Trp Phe Trp Asp Gln His Met Asp Ser Ser
1               5                   10                  15

Thr Ser Ala

<210> SEQ ID NO 3
<211> LENGTH: 19
<212> TYPE: PRT
<213> ORGANISM: Artificial Sequence
<220> FEATURE:
<223> OTHER INFORMATION: synthetic S-tags

<400> SEQUENCE: 3

Lys Glu Thr Gly Trp Ala Leu Phe Val Gln Gln His Met Asp Ser Ser
1               5                   10                  15

Thr Ser Ala

<210> SEQ ID NO 4
<211> LENGTH: 19
<212> TYPE: PRT
<213> ORGANISM: Artificial Sequence
```

```
<220> FEATURE:
<223> OTHER INFORMATION: synthetic S-tags

<400> SEQUENCE: 4

Lys Glu Thr Val Met Ala Asn Phe Gln Met Gln His Met Asp Ser Ser
 1               5                  10                  15

Thr Ser Ala

<210> SEQ ID NO 5
<211> LENGTH: 19
<212> TYPE: PRT
<213> ORGANISM: Artificial Sequence
<220> FEATURE:
<223> OTHER INFORMATION: synthetic S-tags

<400> SEQUENCE: 5

Lys Glu Thr Gly Asp Ala Val Phe Ala Arg Gln His Met Asp Ser Ser
 1               5                  10                  15

Thr Ser Ala

<210> SEQ ID NO 6
<211> LENGTH: 19
<212> TYPE: PRT
<213> ORGANISM: Artificial Sequence
<220> FEATURE:
<223> OTHER INFORMATION: synthetic S-tags

<400> SEQUENCE: 6

Lys Glu Thr Gly Trp Ala Ala Phe Val Lys Gln His Met Asp Ser Ser
 1               5                  10                  15

Thr Ser Ala

<210> SEQ ID NO 7
<211> LENGTH: 19
<212> TYPE: PRT
<213> ORGANISM: Artificial Sequence
<220> FEATURE:
<223> OTHER INFORMATION: synthetic S-tags

<400> SEQUENCE: 7

Lys Glu Thr Gly Trp Ala Thr Phe Val Glu Gln His Met Asp Ser Ser
 1               5                  10                  15

Thr Ser Ala

<210> SEQ ID NO 8
<211> LENGTH: 19
<212> TYPE: PRT
<213> ORGANISM: Artificial Sequence
<220> FEATURE:
<223> OTHER INFORMATION: synthetic S-tags

<400> SEQUENCE: 8

Lys Glu Thr Lys Leu Ala Phe Phe Leu Lys Gln His Met Asp Ser Ser
 1               5                  10                  15

Thr Ser Ala

<210> SEQ ID NO 9

<400> SEQUENCE: 9

000

<210> SEQ ID NO 10
```

<211> LENGTH: 19
<212> TYPE: PRT
<213> ORGANISM: Artificial Sequence
<220> FEATURE:
<223> OTHER INFORMATION: synthetic S-tags

<400> SEQUENCE: 10

Lys Glu Thr Trp Trp Ala Trp Phe Phe Gly Gln His Met Asp Ser Ser
1               5                   10                  15

Thr Ser Ala

<210> SEQ ID NO 11
<211> LENGTH: 19
<212> TYPE: PRT
<213> ORGANISM: Artificial Sequence
<220> FEATURE:
<223> OTHER INFORMATION: synthetic S-tags

<400> SEQUENCE: 11

Lys Glu Thr Thr Trp Ala Glu Phe Thr Trp Gln His Met Asp Ser Ser
1               5                   10                  15

Thr Ser Ala

<210> SEQ ID NO 12
<211> LENGTH: 19
<212> TYPE: PRT
<213> ORGANISM: Artificial Sequence
<220> FEATURE:
<223> OTHER INFORMATION: synthetic S-tags

<400> SEQUENCE: 12

Lys Glu Thr Pro Trp Ala Ser Phe Asn Lys Gln His Met Asp Ser Ser
1               5                   10                  15

Thr Ser Ala

<210> SEQ ID NO 13
<211> LENGTH: 19
<212> TYPE: PRT
<213> ORGANISM: Artificial Sequence
<220> FEATURE:
<223> OTHER INFORMATION: synthetic S-tags

<400> SEQUENCE: 13

Lys Glu Thr Ala Met Ala Met Phe Val Thr Gln His Met Asp Ser Ser
1               5                   10                  15

Thr Ser Ala

<210> SEQ ID NO 14
<211> LENGTH: 19
<212> TYPE: PRT
<213> ORGANISM: Artificial Sequence
<220> FEATURE:
<223> OTHER INFORMATION: synthetic S-tags

<400> SEQUENCE: 14

Lys Glu Thr Leu Trp Ala Trp Phe Met Trp Gln His Met Asp Ser Ser
1               5                   10                  15

Thr Ser Ala

<210> SEQ ID NO 15
<211> LENGTH: 31
<212> TYPE: PRT
<213> ORGANISM: Artificial Sequence
<220> FEATURE:

```
<223> OTHER INFORMATION: CFTR cystic fibrosis transporter

<400> SEQUENCE: 15

Leu Trp Leu Leu Gly Asn Thr Pro Leu Gln Asp Lys Gly Asn Ser Thr
 1               5                  10                  15

His Ser Arg Asn Asn Ser Tyr Ala Val Ile Ile Thr Ser Thr Ser
            20                  25                  30

<210> SEQ ID NO 16
<211> LENGTH: 29
<212> TYPE: PRT
<213> ORGANISM: Artificial Sequence
<220> FEATURE:
<223> OTHER INFORMATION: CFTR cystic fibrosis transporter

<400> SEQUENCE: 16

Ser Ala Ser Gly Gly Gly Gly Lys Glu Thr Ala Ala Ala Lys Phe Glu
 1               5                  10                  15

Arg Gln His Met Asp Ser Gly Gly Gly Gly Thr Arg Thr
            20                  25

<210> SEQ ID NO 17
<211> LENGTH: 48
<212> TYPE: PRT
<213> ORGANISM: Artificial Sequence
<220> FEATURE:
<223> OTHER INFORMATION: CFTR cystic fibrosis transporter

<400> SEQUENCE: 17

Ser Ala Ser Gly Gly Gly Gly Lys Glu Thr Ala Ala Ala Lys Phe Glu
 1               5                  10                  15

Arg Gln His Met Asp Ser Gly Gly Gly Gly Lys Glu Thr Ala Ala Ala
            20                  25                  30

Lys Phe Glu Arg Gln His Met Asp Ser Gly Gly Gly Gly Thr Arg Thr
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: CFTR cystic fibrosis transporter

<400> SEQUENCE: 18

Ser Ala Ser Gly Gly Gly Gly Lys Glu Thr Ala Ala Ala Lys Phe Glu
 1               5                  10                  15

Arg Gln His Met Asp Ser Gly Gly Gly Gly Lys Glu Thr Ala Ala Ala
            20                  25                  30

Lys Phe Glu Arg Gln His Met Asp Ser Gly Gly Gly Gly Pro Arg Thr
        35                  40                  45

<210> SEQ ID NO 19
<211> LENGTH: 67
<212> TYPE: PRT
<213> ORGANISM: Artificial Sequence
<220> FEATURE:
<223> OTHER INFORMATION: CFTR cystic fibrosis transporter

<400> SEQUENCE: 19

Ser Ala Ser Gly Gly Gly Gly Lys Glu Thr Ala Ala Ala Lys Phe Glu
 1               5                  10                  15

Arg Gln His Met Asp Ser Gly Gly Gly Gly Lys Glu Thr Ala Ala Ala
            20                  25                  30
```

```
Lys Phe Glu Arg Gln His Met Asp Ser Gly Gly Gly Lys Glu Thr
        35                  40                  45

Ala Ala Ala Lys Phe Glu Arg Gln His Met Asp Ser Gly Gly Gly Gly
 50                  55                  60

Pro Arg Thr
 65

<210> SEQ ID NO 20
<211> LENGTH: 86
<212> TYPE: PRT
<213> ORGANISM: Artificial Sequence
<220> FEATURE:
<223> OTHER INFORMATION: CFTR cystic fibrosis transporter

<400> SEQUENCE: 20

Ser Ala Ser Gly Gly Gly Gly Lys Glu Thr Ala Ala Ala Lys Phe Glu
 1               5                  10                  15

Arg Gln His Met Asp Ser Gly Gly Gly Lys Glu Thr Ala Ala Ala
            20                  25                  30

Lys Phe Glu Arg Gln His Met Asp Ser Gly Gly Gly Lys Glu Thr
        35                  40                  45

Ala Ala Ala Lys Phe Glu Arg Gln His Met Asp Ser Gly Gly Gly Gly
 50                  55                  60

Lys Glu Thr Ala Ala Ala Lys Phe Glu Arg Gln His Met Asp Ser Gly
 65                  70                  75                  80

Gly Gly Pro Arg Thr
            85

<210> SEQ ID NO 21
<211> LENGTH: 28
<212> TYPE: PRT
<213> ORGANISM: Artificial Sequence
<220> FEATURE:
<223> OTHER INFORMATION: CFTR cystic fibrosis transporter

<400> SEQUENCE: 21

Ser Ala Ser Ser Gly Lys Glu Thr Ala Ala Ala Lys Phe Glu Arg Gln
 1               5                  10                  15

His Met Asp Ser Pro Pro Pro Ser Gly Thr Arg Thr
            20                  25

<210> SEQ ID NO 22
<211> LENGTH: 26
<212> TYPE: PRT
<213> ORGANISM: Artificial Sequence
<220> FEATURE:
<223> OTHER INFORMATION: CFTR cystic fibrosis transporter

<400> SEQUENCE: 22

Ser Ala Ser Ser Gly Lys Glu Thr Ala Ala Ala Lys Phe Glu Arg Gln
 1               5                  10                  15

His Met Asp Ser Pro Pro Pro Ser Gly Leu
            20                  25

<210> SEQ ID NO 23
<211> LENGTH: 27
<212> TYPE: PRT
<213> ORGANISM: Artificial Sequence
<220> FEATURE:
<223> OTHER INFORMATION: CFTR cystic fibrosis transporter

<400> SEQUENCE: 23
```

```
Ser Ala Ser Gly Met Lys Glu Thr Ala Ala Lys Phe Glu Arg Gln
1               5                  10                  15

His Met Asp Ser Pro Asp Leu Gly Thr Arg Thr
            20                  25

<210> SEQ ID NO 24
<211> LENGTH: 25
<212> TYPE: PRT
<213> ORGANISM: Artificial Sequence
<220> FEATURE:
<223> OTHER INFORMATION: CFTR cystic fibrosis transporter

<400> SEQUENCE: 24

Thr Leu Gln Asp Asp Lys Glu Thr Ala Ala Ala Lys Phe Glu Arg Gln
1               5                  10                  15

His Met Asp Ser Asp Asp Pro Gly His
            20                  25

<210> SEQ ID NO 25
<211> LENGTH: 27
<212> TYPE: PRT
<213> ORGANISM: Artificial Sequence
<220> FEATURE:
<223> OTHER INFORMATION: CFTR cystic fibrosis transporter

<400> SEQUENCE: 25

Thr Leu His Gly Asp Asp Lys Glu Thr Ala Ala Ala Lys Phe Glu Arg
1               5                  10                  15

Gln His Met Asp Ser Asp Asp Gly Ser Gly His
            20                  25

<210> SEQ ID NO 26
<211> LENGTH: 46
<212> TYPE: PRT
<213> ORGANISM: Artificial Sequence
<220> FEATURE:
<223> OTHER INFORMATION: CFTR cystic fibrosis transporter

<400> SEQUENCE: 26

Thr Leu His Gly Asp Asp Lys Glu Thr Ala Ala Ala Lys Phe Glu Arg
1               5                  10                  15

Gln His Met Asp Ser Gly Asp Asp Gly Lys Glu Thr Ala Ala Ala Lys
            20                  25                  30

Phe Glu Arg Gln His Met Asp Ser Asp Asp Gly Ser Gly His
        35                  40                  45

<210> SEQ ID NO 27
<211> LENGTH: 67
<212> TYPE: PRT
<213> ORGANISM: Artificial Sequence
<220> FEATURE:
<223> OTHER INFORMATION: CFTR cystic fibrosis transporter

<400> SEQUENCE: 27

Thr Ala Ser Gly Gly Gly Gly Lys Glu Thr Ala Ala Ala Lys Phe Glu
1               5                  10                  15

Arg Gln His Met Asp Ser Gly Gly Gly Lys Glu Thr Ala Ala Ala
            20                  25                  30

Lys Phe Glu Arg Gln His Met Asp Ser Gly Gly Gly Lys Glu Thr
        35                  40                  45

Ala Ala Ala Lys Phe Glu Arg Gln His Met Asp Ser Gly Gly Gly Gly
    50                  55                  60
```

Pro Arg His
65

<210> SEQ ID NO 28
<211> LENGTH: 72
<212> TYPE: PRT
<213> ORGANISM: Artificial Sequence
<220> FEATURE:
<223> OTHER INFORMATION: CFTR cystic fibrosis transporter

<400> SEQUENCE: 28

Thr Leu His Gly Asp Asp Lys Glu Thr Ala Ala Ala Lys Phe Glu Arg
1               5                   10                  15

Gln His Met Asp Ser Gly Asp Asp Gly Lys Glu Thr Ala Ala Ala Lys
            20                  25                  30

Phe Glu Arg Gln His Met Asp Ser Gly Asp Asp Glu Lys Lys Gln Gln
        35                  40                  45

Gln Gln Asn Leu Lys Asp Asn Thr Trp Ile Ala Met Met Asp Pro Gly
    50                  55                  60

Ile Val Glu Ile Thr Ala Met Gln
65                  70

<210> SEQ ID NO 29
<211> LENGTH: 41
<212> TYPE: PRT
<213> ORGANISM: Artificial Sequence
<220> FEATURE:
<223> OTHER INFORMATION: CFTR cystic fibrosis transporter

<400> SEQUENCE: 29

Thr Leu His Gly Asp Lys Glu Thr Ala Trp Ala Lys Phe Glu Asp Gln
1               5                   10                  15

His Met Asp Ser Gly Lys Glu Thr Ala Trp Ala Lys Phe Glu Asp Gln
            20                  25                  30

His Met Asp Ser Asp Gly Ser Gly His
        35                  40

<210> SEQ ID NO 30
<211> LENGTH: 57
<212> TYPE: PRT
<213> ORGANISM: Artificial Sequence
<220> FEATURE:
<223> OTHER INFORMATION: CFTR cystic fibrosis transporter

<400> SEQUENCE: 30

Thr Leu His Gly Asp Lys Glu Thr Ala Trp Ala Lys Phe Glu Asp Gln
1               5                   10                  15

His Met Asp Ser Gly Lys Glu Thr Ala Trp Ala Lys Phe Glu Asp Gln
            20                  25                  30

His Met Asp Ser Gly Lys Glu Thr Ala Trp Ala Lys Phe Glu Asp Gln
        35                  40                  45

His Met Asp Ser Asp Gly Ser Gly His
    50                  55

<210> SEQ ID NO 31
<211> LENGTH: 25
<212> TYPE: PRT
<213> ORGANISM: Artificial Sequence
<220> FEATURE:
<223> OTHER INFORMATION: CFTR cystic fibrosis transporter

<400> SEQUENCE: 31

Thr Leu His Gly Asp Lys Glu Thr Ala Trp Ala Lys Phe Glu Asp Gln
1               5                   10                  15

His Met Asp Ser Asp Gly Ser Gly His
            20                  25

<210> SEQ ID NO 32
<211> LENGTH: 41
<212> TYPE: PRT
<213> ORGANISM: Artificial Sequence
<220> FEATURE:
<223> OTHER INFORMATION: CFTR cystic fibrosis transporter

<400> SEQUENCE: 32

Thr Leu His Gly Asp Lys Glu Thr Ala Trp Ala Glu Phe Glu Arg Gln
1               5                   10                  15

His Met Asp Ser Gly Lys Glu Thr Ala Trp Ala Glu Phe Glu Arg Gln
            20                  25                  30

His Met Asp Ser Asp Gly Ser Gly His
        35                  40

<210> SEQ ID NO 33
<211> LENGTH: 41
<212> TYPE: PRT
<213> ORGANISM: Artificial Sequence
<220> FEATURE:
<223> OTHER INFORMATION: CFTR cystic fibrosis transporter

<400> SEQUENCE: 33

Thr Leu His Gly Asp Lys Glu Thr Ala Trp Ala Glu Phe Glu Asp Gln
1               5                   10                  15

His Met Asp Ser Gly Lys Glu Thr Ala Trp Ala Glu Phe Glu Asp Gln
            20                  25                  30

His Met Asp Ser Asp Gly Ser Gly His
        35                  40

<210> SEQ ID NO 34
<211> LENGTH: 21
<212> TYPE: PRT
<213> ORGANISM: Artificial Sequence
<220> FEATURE:
<223> OTHER INFORMATION: CFTR cystic fibrosis transporter

<400> SEQUENCE: 34

His Ser Leu Glu Lys Glu Thr Ala Ala Ala Lys Phe Glu Arg Gln His
1               5                   10                  15

Met Asp Ser Ala Ser
            20

<210> SEQ ID NO 35
<211> LENGTH: 29
<212> TYPE: PRT
<213> ORGANISM: Artificial Sequence
<220> FEATURE:
<223> OTHER INFORMATION: CFTR cystic fibrosis transporter

<400> SEQUENCE: 35

His Ala Ser Gly Gly Gly Gly Lys Glu Thr Ala Ala Ala Lys Phe Glu
1               5                   10                  15

Arg Gln His Met Asp Ser Gly Gly Gly Gly Thr Arg Ser
            20                  25

<210> SEQ ID NO 36

<211> LENGTH: 67
<212> TYPE: PRT
<213> ORGANISM: Artificial Sequence
<220> FEATURE:
<223> OTHER INFORMATION: CFTR cystic fibrosis transporter

<400> SEQUENCE: 36

His Ala Ser Gly Gly Gly Lys Glu Thr Ala Ala Ala Lys Phe Glu
1               5                   10                  15

Arg Gln His Met Asp Ser Gly Gly Gly Lys Glu Thr Ala Ala Ala
                20                  25                  30

Lys Phe Glu Arg Gln His Met Asp Ser Gly Gly Gly Lys Glu Thr
            35                  40                  45

Ala Ala Ala Lys Phe Glu Arg Gln His Met Asp Ser Gly Gly Gly Gly
        50                  55                  60

Pro Arg Ser
65

<210> SEQ ID NO 37
<211> LENGTH: 28
<212> TYPE: PRT
<213> ORGANISM: Artificial Sequence
<220> FEATURE:
<223> OTHER INFORMATION: CFTR cystic fibrosis transporter

<400> SEQUENCE: 37

His Ala Ser Ser Gly Lys Glu Thr Ala Ala Ala Lys Phe Glu Arg Gln
1               5                   10                  15

His Met Asp Ser Pro Pro Pro Ser Gly Thr Arg Ser
            20                  25

<210> SEQ ID NO 38
<211> LENGTH: 26
<212> TYPE: PRT
<213> ORGANISM: Artificial Sequence
<220> FEATURE:
<223> OTHER INFORMATION: CFTR cystic fibrosis transporter

<400> SEQUENCE: 38

His Ala Ser Ser Gly Lys Glu Thr Ala Ala Ala Lys Phe Glu Arg Gln
1               5                   10                  15

His Met Asp Ser Pro Pro Pro Ser Gly Leu
            20                  25

<210> SEQ ID NO 39
<211> LENGTH: 27
<212> TYPE: PRT
<213> ORGANISM: Artificial Sequence
<220> FEATURE:
<223> OTHER INFORMATION: CFTR cystic fibrosis transporter

<400> SEQUENCE: 39

His Ala Ser Gly Met Lys Glu Thr Ala Ala Ala Lys Phe Glu Arg Gln
1               5                   10                  15

His Met Asp Ser Pro Asp Leu Gly Thr Arg Ser
            20                  25

<210> SEQ ID NO 40
<211> LENGTH: 17
<212> TYPE: PRT
<213> ORGANISM: Artificial Sequence
<220> FEATURE:
<223> OTHER INFORMATION: CFTR cystic fibrosis transporter -continued

```
<400> SEQUENCE: 40

Ser Lys Glu Thr Ala Ala Ala Lys Phe Glu Arg Gln His Met Asp Ser
1               5                   10                  15

Tyr

<210> SEQ ID NO 41
<211> LENGTH: 67
<212> TYPE: PRT
<213> ORGANISM: Artificial Sequence
<220> FEATURE:
<223> OTHER INFORMATION: CFTR cystic fibrosis transporter

<400> SEQUENCE: 41

Ser Ala Ser Gly Gly Gly Lys Glu Thr Ala Ala Ala Lys Phe Glu
1               5                   10                  15

Arg Gln His Met Asp Ser Gly Gly Gly Lys Glu Thr Ala Ala Ala
                20                  25                  30

Lys Phe Glu Arg Gln His Met Asp Ser Gly Gly Gly Lys Glu Thr
            35                  40                  45

Ala Ala Ala Lys Phe Glu Arg Gln His Met Asp Ser Gly Gly Gly Gly
        50                  55                  60

Pro Arg Tyr
65
```

COMPOSITIONS AND METHODS FOR HIGH THROUGHPUT SCREENING OF PHARMACOLOGICAL CHAPERONES

FEDERALLY-SPONSORED RESEARCH OR DEVELOPMENT

This invention was made with Government support under contract AG023608 awarded by the National Institutes of Health. The Government has certain rights in this invention.

BACKGROUND OF THE INVENTION

Many inherited diseases; including cystic fibrosis, diabetes, and familial hypercholesterolemia are caused by mutations that impair the folding and intracellular trafficking of ion channels, transporters and receptors that are normally expressed at the plasma membrane. There is compelling evidence demonstrating that the mutant phenotype of many of these mutants can be suppressed by treatment with pharmacological chaperones, which are small high affinity ligands that bind to and stabilize the native 3-dimensional structure of their respective targets.

Prion diseases like Scrapie (sheep), bovine spongiform encephalopathy (BSE, cattle), or Creutzfeldt-Jakob disease (CJD, human), and other neurodegenerative diseases such as Parkinson and Alzheimer, are the result of precipitated protein aggregates. On the other hand, human diseases such as cystic fibrosis and lung emphysema are caused by the rapid disappearance of crucial proteins, like the cystic fibrosis transmembrane conductance regulator (CFTR) and α-1-antitrypsin, respectively. The discovery of the degradation process for mutated and misfolded ER proteins has shed light on the molecular mechanism underlying such seemingly different diseases.

It is of great importance for the cell to regulate the individual entities of its proteome as well as to control the structural fidelity of each of its members. Proteins destined for secretion, the plasma membrane or the cell surface are translocated from the cytoplasm into the endoplasmic reticulum (ER), the central organelle for further delivery of these proteins to their site of action. Since proteins are translocated into the ER in an unfolded state, it is the primary function of this organelle to modify and fold the translocated proteins to acquire their biologically active conformation. In the ER, proteins undergo a quality control procedure that discriminates between properly folded proteins and terminally misfolded species as well as unassembled protein subunits. The misfolded polypeptides and orphan subunits are subsequently subjected to ER-associated degradation (ERAD). The ERAD process requires retrotranslocation of the malfolded proteins across the ER membrane into the cytoplasm and subsequent degradation by the proteasome. ER degradation contributes to the molecular pathogenesis of many loss- and gain-of-toxic-function disorders.

In the ER lumen, polypeptides can be modified by a large array of ER-resident chaperones and enzymes, before they can enter the secretory pathway. The major components of this process in the ER are signal peptidase, which cleaves off the signal peptide from the newly translocated proteins; the oligosaccaryl-transferase complex (OST) which carries out N-glycosylation; and protein disulfide isomerase (PDI), which participates in disulfide bond formation. The two most studied examples of chaperones that assist proteins in their folding are the Hsp70 chaperone BiP, which recognizes hydrophobic patches on proteins, and calnexin, which binds carbohydrate moieties. Proteins are allowed to exit the ER and enter the secretory pathway only when they are properly folded and modified.

The quality control mechanism works by structural rather than functional criteria. Mutations in CFTR and α-1-antitrypsin, for example, which do not perturb the biological activity of the proteins per se, lead to ER retention and elimination of the mutant molecules, thus causing disease. In a series of glycosylation events, proteins are marked during the folding process. Recognition of the carbohydrate residues on misfolded proteins determines their delivery to the elimination machinery.

Nearly all misfolded proteins are polyubiquitylated prior to degradation. It has been suggested that polyubiquitylation is necessary for retrotranslocation. Modification of the protein may occur when the N-terminus or the first lysine residue becomes accessible to the ubiquitylation machinery. Progressive polyubiquitylation may serve as a ratcheting mechanism moving the polypeptide from the retrotranslocation channel into the cytoplasm, where the long and bulky polyubiquitin chains prevent the polypeptide from slipping back into the ER. The proteasome acts after release of the ubiquitylated substrate from the ER membrane. It is currently believed that Rpn11 de-ubiquitylates the substrate after it has been threaded into the 20S channel, thereby resulting in an irreversible commitment to proteolysis. Failure to de-ubiquitylate probably causes a sterical block to further insertion of the substrate into the proteolytic core. Following release from the substrate, the polyubiquitin chain is hydrolyzed into single ubiquitin moieties which can take part in a new round of protein degradation.

Cystic fibrosis (CF), a fatal autosomal recessive genetic disease that affects over 60,000 people worldwide, is caused by mutations in CFTR. This gene encodes the cystic fibrosis transmembrane conductance regulator protein, which functions as a Cl⁻ channel at the apical membranes of pulmonary epithelial cells. The CFTR channel is also found in certain other epithelia, such as the sweat ducts and part of the gastrointestinal tract, but lung pathology is by far the most prominent cause of clinical disease in CFTR homozygotes and compound heterozygotes. Precisely how the loss of functional, surface-expressed CFTR channels and the consequent decrease in Cl⁻ conductance lead to CF pathogenesis is controversial. Still, the recognition that the majority of cases of CF are the result of a defect in biogenesis or intracellular trafficking of the protein, and that the mutant protein retains at least partial function, has stimulated an intensive search for therapeutic-strategies aimed at rescuing the function of the mutant CFTR.

In view of the many serious medical conditions associated with misfolded proteins, methods of high throughput screening for agents that ameliorate these conditions are of interest. The present invention addresses these issues.

SUMMARY OF THE INVENTION

Flexible multiplex screening assays are provided for the screening and classification of biologically active agents that alter the conformation of conformationally defective proteins, particularly during synthesis of the protein. A conformationally defective protein of interest is engineered to comprise one or more S-tag sequences. Cells expressing the S-tagged protein are contacted with candidate biologically active agents. Following a period of time sufficient for expression, the cells are contacted with extracellular RNAse S and a substrate for detection of enzymatic activity. In the presence of agents or conditions that are sufficient to stabilize the S-tagged protein and allow it to reach the cell surface, the RNAse is complemented, and activity is detected by cleavage of the substrate.

The methods of the invention find use in the identification and classification of agents with chaperone activity, particularly the identification and classification of small molecule chemical and pharmacological chaperones. The agents thus identified find use altering the conformation of otherwise conformationally defective proteins.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
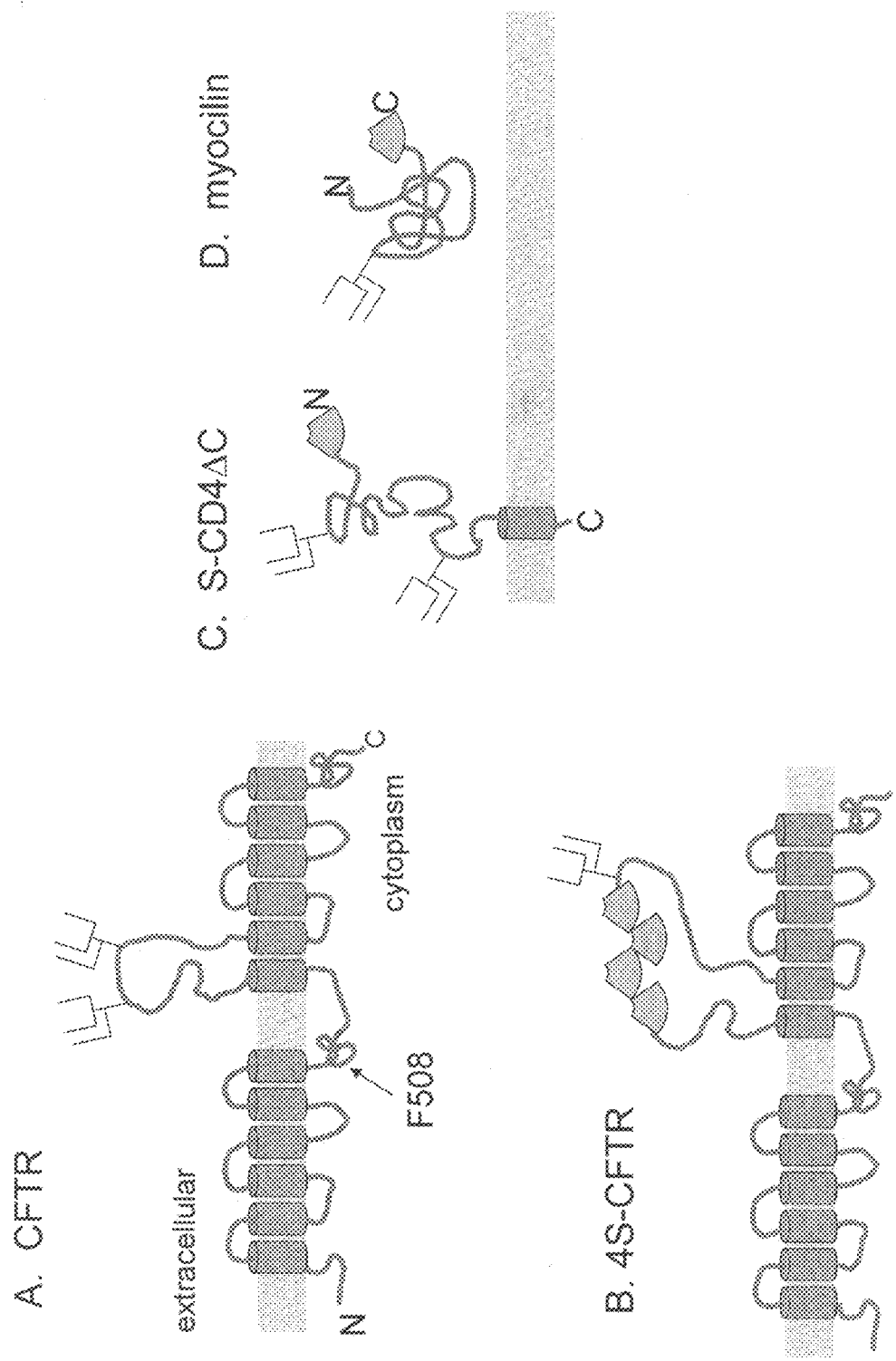
FIG. 1A-1D. Cartoon depiction of topology of proteins used in this study. (A) Cystic fibrosis transmembrane conductance regulator (CFTR). Location of phenylalanine 508 and sites of N-linked glycosylation are indicated. (B) CFTR construct tagged with 4 tandemly repeated S-peptides in the 4'th extracellular loop. Note that the amino-terminal N-glycosylation site is ablated. (C). A mutant form of the T-cell CD4 surface protein lacking the C-terminal cytoplasmic domain was tagged with a single S-peptide immediately following the N-terminal cleaved signal sequence. (D). Myocilin tagged at its C-terminus with S-peptide is not membrane-associated.

Flexible multiplex screening assays are provided for the screening and classification of biologically active agents that alter protein conformation. Proteins of interest for screening include those encoded by the large number of disease-associated alleles that lead to the production of conformationally defective proteins. Proteins of interest for the methods of the invention include polytopic integral membrane proteins, e.g. ion channels, transporters, receptors, and the like, and secreted proteins, which must be folded in the context of the cellular biogenesis machinery.

Both recessively and dominantly inherited diseases are known to be linked to mutations that impair the ability of a protein to achieve a stable native 3-dimensional structure, and thus have been classified as conformational diseases. The clinical features of conformational disease can be suppressed by chemical or pharmacological chaperones, which are biologically active agents that enhance the folding and/or stability of the mutant proteins.

The methods of the present invention provide a cell-based platform to identify agents that directly enhance the folding and/or stability of mutant integral membrane proteins and secreted proteins. The methods of the invention utilize enzymatic complementation of RNAse to detect the presence of mutant proteins that are sufficiently stabilized and/or folded so as to escape ER degradation, and which are therefore present on the cell surface, or secreted into the extracellular medium. The assays of the invention can detect very low levels of expression of the tagged protein at the cell surface. The context independent tag does not influence the folding or trafficking of the reporter protein. The assay provides extremely high signal-to-noise and low background from non-specifically bound probe, with a calorimetric or fluorogenic readout amenable to robotic high-throughput detection, and requires minimal manipulation or disturbance of reporter cells.

In the methods of the invention, a conformationally defective protein is engineered to comprise one or more S-tag sequences. The one or more S-tag sequences are inserted at a site in the protein sequence that is accessible on the cell surface; that does not interfere with the protein folding, and that permits complementation with extracellular RNAse S. The protein thus engineered is expressed in a cell-based assay. The cells expressing the S-tagged protein are contacted with candidate biologically active agents. Following a period of time sufficient for expression, the cells are contacted with extracellular RNAse S and a substrate for detection of enzymatic activity. In the presence of agents or conditions that are sufficient to stabilize the S-tagged protein and allow it to reach the cell surface, the RNAse is complemented, and activity is detected by cleavage of the substrate. In some embodiments of the invention, the S-tagged protein is CFTR, where one or more S-tag sequences are inserted in the 4th extracellular loop.

Folding, as used herein, refers to the three-dimensional structure of polypeptides and proteins or the process of attaining such a structure, where interactions between amino acid residues act to stabilize the structure. While non-covalent interactions are important in determining structure, usually the peptides and proteins of interest will have intra- and/or intermolecular covalent bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc. For the purposes of the present invention, a marker for proper folding is used, in that the protein is secreted or expressed on the cell surface, i.e. the protein escapes ER-associated degradation.

Enzymatic complementation of RNAse. Ribonuclease A proteins are known in the art to be capable of being cleaved into two inactive fragments the S tag, and S-protein. For example, when native bovine Ribonuclease A is cleaved by mild proteolysis with subtilisin, two fragments are generated, an N-terminal peptide (S-peptide, 15 amino acids) and an S-protein (104 amino acids). These fragments have a high affinity for one another and they remain associated in the cleaved enzyme, which is called ribonuclease S. The two fragments can be separated at low pH, thereby inactivating the enzyme and activity can be restored by adding them back together at neutral pH. Recombinant S-protein has no enzymatic activity nor does synthetic S-peptide, but the two can be reconstituted to form an RNAse S molecule in vitro. In other words, proteins comprising an S tag sequence have no RNAse activity in the absence of the complementary fragment, and in the absence of the S-tag, enzymatic activity of S-protein is completely undetectable.

Binding of S-peptide to a protein comprising an S-tag is detected by monitoring reconstitution of RNAase activity. Such methods provide for very low background. Although the S-protein may bind non-specifically to the cell surface, such binding events do not reconstitute enzymatic activity, and therefore are silent. Because the detection system depends on enzymatic cleavage of a substrate, the sensitivity of the assay can be boosted by enzymatic amplification of the signal. The entire reaction can be performed by a single manipulation of the cells by the addition of substrate and enzymatically inactive S-protein.

A number of RNAse A proteins are known and well characterized in the art, for example see Moore and Stein (1973) Science 180, 458-464; Beintema et al. (1986) Mol Biol Evol. 3(3):262-75, herein specifically incorporated by reference for the teaching of RNAse A sequences. As used herein, the term RNAse A refers to a pancreatic type ribonuclease, typically of a mammalian species, as provided in the above references, or as set forth in the exemplary sequences: bovine, accession AAB35594; human, accession NP_002924.1; chimpanzee, accession XP_520673.1; canine, accession number XP_532618.2; mouse, accession number NP_035401.2; rat, accession number XP_223969.2; and the like, or a derivative thereof having RNAse activity and a sequence that is at least about 90% identical to any one of the provided sequences; at least about 95% identical to any one of the provided sequences; at least about 99% identical to any one of the provided sequences, or more. As is known in the art, the S-protein fragment may be recombinantly produced, enzymatically cleaved, etc. to generate an inactive fragment that has a high affinity for the S-tag, and which is complemented by the S-tag to generate an active enzyme.

The S-tag subunit typically comprises around about 17-21 amino acids from the terminus of the RNAse A. Exemplary sequences include the wild-type S-tag of bovine RNAse A: (SEQ ID NO:1) KETAAAKFERQHMDSSTSA. S-tag sequences can be varied, for example see Backer et al. (2002) Protein Expression and Purification 26 (2002) 455-461; and Dwyer et al. 2001 Biochemistry. 40(45):13491-500, herein incorporated by reference for the teaching of S-peptide variants. Variant S-peptide sequences include (SEQ ID NO:2) KETNWAWFWDQHMDSSTSA; (SEQ ID NO:3) KETGWALFVQQHMDSSTSA; (SEQ ID NO:4) KETVMANFQMQHMDSSTSA; (SEQ ID NO:5) KETGDAVFARQHMDSSTSA; (SEQ ID NO:6) KETGWAAFVKQHMDSSTSA; (SEQ ID NO:7) KETGWATFVEQHMDSSTSA; (SEQ ID NO:8) KETKLAFFLKQHMDSSTSA; (SEQ ID NO:9); (SEQ ID NO:10) KETWWAWFFGQHMDSSTSA; (SEQ ID NO:11) KETTWAEFTWQHMDSSTSA; (SEQ ID NO:12) KETPWASFNKQHMDSSTSA; (SEQ ID NO:13) KETAMAMFVTQHMDSSTSA; and (SEQ ID NO:14) KETLWAWFMWQHMDSSTSA. The S-peptide has no detectable secondary structure, extremely high solubility, and no net charge at neutral pH, properties which explain its general lack of influence on the folding or function of the target proteins to which it has been fused.

The RNAse S detector protein may be produced by methods known to those of skill in the art, or is commercially available. Substrates for detection of RNAse activity are also widely available. Such substrates are also commercially available. In one embodiment of the invention the substrate is a mixed polynucleotide of ribonucleotides and deoxyribonucleotides.

Labeled substrate. A cleavable ribonucleic acid molecule (or mixed polynucleotide of ribonucleotides and deoxyribonucleotides), comprising a detectable label. The substrate may be an RNA molecule, or may be a molecule comprising an RNA linkage, e.g. PNA, nucleic acid analogs, DNA, etc., where one or more of the nucleoside linkages is cleavable with RNAse. Detectable labels include isotopic labels, in which one or more of the nucleotides is labeled with a radioactive label, such as $^{35}S$, $^{32}P$, $^3H$, etc. Fluorescent labels of interest include: fluorescein, rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), the cyanine dyes, such as Cy3, Cy5, Alexa 542, Bodipy 630/650, fluorescent particles, fluorescent semiconductor nanocrystals, and the like.

In one embodiment of the invention, the label is undetectable until cleavage, e.g. in a donor/quencher pair, and the reaction vessel is monitored for a change in fluorescence resulting from cleavage.

In one embodiment, the substrate is a self-quenching fluorescence substrate comprising a reporter dye and a quencher dye (donor-quencher pair). Upon RNAse cleavage of the ribonucleotides in the probe, the fluorescer and quencher separate so that a fluorescent signal is detectable. The probe is designed so as to bring the reporter into close proximity with the quencher, which permits efficient energy transfer from the reporter to the quencher. A donor-quencher pair comprises two fluorophores having overlapping spectra, where the donor emission overlaps the acceptor absorption, so that there is energy transfer from the excited fluorophore to the other member of the pair. It is not essential that the excited fluorophore actually fluoresce, it being sufficient that the excited fluorophore be able to efficiently absorb the excitation energy and efficiently transfer it to the emitting fluorophore.

The donor fluorophore is excited efficiently by a single light source of narrow bandwidth, particularly a laser source. The emitting or accepting fluorophors will be selected to be able to receive the energy from the donor fluorophore and emit light. Usually the donor fluorophores will absorb in the range of about 350-800 nm, more usually in the range of about 350-600 nm or 500-750 nm, while the acceptor fluorophores will emit light in the range of about 450-1000 nm, usually in the range of about 450-800 nm.

The two fluorophores will be joined by an RNAse cleavable bond, which may be provided as an RNA polynucleotide, where the distance between the two fluorophores may be varied. The transfer of the optical excitation from the donor to the acceptor depends on the distance between the two fluorophores. Thus, the distance must be chosen to provide efficient energy transfer from the donor to the acceptor. Various conventional chemistries may be employed to ensure that the appropriate spacing between the two fluorophores is obtained. The fluorophores may be bound internal to the chain, at the termini, or one at one terminus and another at an internal site.

The fluorophores may be selected so as to be from a similar chemical family or a different one, such as cyanine dyes, xanthenes or the like. Reporter, or donor, dyes of interest include: fluorescein dyes (e.g., 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyfluorescein (JOE)), cyanine dyes, dansyl derivatives, and the like. Quencher dyes of interest include: rhodamine dyes (e.g., tetramethyl-6-carboxyrhodamine (TAMRA), and tetrapropano-6-carboxyrhodamine (ROX)), DABSYL, DABCYL, cyanine, anthraquinone, nitrothiazole, and nitroimidazole compounds, and the like. The labeled RNA probe can be produced using any convenient protocol. Cleavage of the RNA by the active RNAse enzyme results in a change of detectable signal, which may be disappearance or appearance of label, e.g. fluorescence.

In some embodiments, RNAase activity is assayed using an optimized tetranucleotide substrate dArUdAdA, which incorporates a ribonucleotide at position 2 and deoxyribonucleotides at positions 1, 3, and 4. This substrate was optimized for interaction with RNAase A, and displays a $10^5$ fold higher $K_{cat}/K_M$ for RNAase A. This oligonucleotide substrate is labeled at the two ends a suitable donor-quencher pair, for example 5',6-carboxyfluorescein (6-F) and 3',6-carboxytetramethylrhodamine (6-TMR).

Expression construct: A conformationally defective S-tagged protein is produced by recombinant methods. DNA encoding the conformationally defective protein of interest may be obtained from various sources as appropriate to the specific protein. Screening cDNA or genomic libraries with the selected probe may be conducted using standard procedures as described in Sambrook et al, Molecular Cloning: A Laboratory Manual (New York: Cold Spring Harbor Laboratory Press, 1989), by PCR methodology, and the like. Introduction of one or more S-tag sequences into the protein of interest may be accomplished by various methods known to those of skill in the art.

The nucleic acid (e.g., cDNA or genomic DNA) encoding the S-tagged polypeptide is inserted into a replicable vector for expression. Many such vectors are available. The vector components generally include, but are not limited to, one or more of the following: an origin of replication, one or more marker genes, an enhancer element, a promoter, and a transcription termination sequence. S-tagged polypeptides will generally utilize the native signal sequence of the conformationally defective protein of interest.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

Expression vectors will contain a promoter that is recognized by the host organism and is operably linked to the S-tagged polypeptide coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Heterologous promoters are preferred, as they generally permit greater transcription and higher yields.

Transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors will usually also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding S-tagged polypeptide.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Suitable host cells for cloning or expressing the DNA in the vectors herein are typically mammalian cells, e.g. HeLa, CHO, etc., as known in the art. The polypeptide of interest may be expressed in a cell type where the protein is normally expressed, e.g. CFTR in epithelial cells; arginine vasopressin in kidney cells, and the like. Alternatively, any suitable mammalian cell line that provides for appropriate folding and quality control mechanisms may be used.

Chemical and pharmacological chaperones and candidate agents. The term "chemical chaperone" describes a family of low-molecular weight compounds including polyols (e.g., glycerol, sorbitol, and myo-inositol), amines (e.g., betaine and trimethylamine-N-oxide [TMAO]), and solvents such as DMSO and $D_2O$. These compounds have been recognized to have protein-stabilizing properties in vitro, due largely to their ability to increase protein hydration. Endogenously produced compounds like myo-inositol and betaine serve as osmolytes, balancing osmotic forces in cells and organisms that are chronically exposed to osmotic stress. Chemical chaperones can stabilize protein conformation by increasing molecular crowding, by enhancing protein hydration and by favoring hydrophobic interactions. However, known chemical chaperones must be present at high concentrations for activity, and at such concentrations they may exert significant osmotic stress.

Pharmacological chaperones are substrates or ligands of cell surface-borne channels and receptors. PCs stabilize the native state of protein conformation by binding tightly to their substrates. High affinity ligands can stabilize the 3-dimensional structure of proteins to which they bind. For example, high affinity binding of the substrate analog methotrexate stabilizes the soluble enzyme dihydrofolate reductase (DHFR). Small molecule ligands can facilitate the folding of folding-defective integral membrane proteins.

Candidate agents of interest are biologically active agents that encompass numerous chemical classes, primarily organic molecules, which may include organometallic molecules, inorganic molecules, genetic sequences, etc. An important aspect of the invention is to evaluate candidate drugs for an effect on translation. Candidate agents comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term "samples" also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Libraries of candidate compounds can also be prepared by rational design. (See generally, Cho et al., *Pac. Symp. Biocompat.* 305-16, 1998); Sun et al., *J. Comput. Aided Mol. Des.* 12:597-604, 1998); each incorporated herein by reference in their entirety). For example, libraries of phosphatase inhibitors can be prepared by syntheses of combinatorial chemical libraries (see generally DeWitt et al., *Proc. Nat. Acad. Sci. USA* 90:6909-13, 1993; International Patent Publication WO 94/08051; Baum, *Chem. & Eng. News*, 72:20-25, 1994; Burbaum et al., *Proc. Nat. Acad. Sci. USA* 92:6027-31, 1995; Baldwin et al., *J. Am. Chem. Soc.* 117:5588-89, 1995; Nestler et al., *J. Org. Chem.* 59:4723-24, 1994; Borehardt et al., *J. Am. Chem. Soc.* 116:373-74, 1994; Ohlmeyer et al., *Proc. Nat. Acad. Sci. USA* 90:10922-26, all of which are incorporated by reference herein in their entirety.)

A "combinatorial library" is a collection of compounds in which the compounds comprising the collection are composed of one or more types of subunits. Methods of making combinatorial libraries are known in the art, and include the following: U.S. Pat. Nos. 5,958,792; 5,807,683; 6,004,617; 6,077,954; which are incorporated by reference herein. The subunits can be selected from natural or unnatural moieties. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules that are different from each other. Each of the different molecules is present in a detectable amount. The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. Substituents are added to the starting compound, and can be varied by providing a mixture of reactants comprising the substituents. Examples of suitable substituents include, but are not limited to, hydrocarbon substituents, e.g. aliphatic, alicyclic substituents, aromatic, aliphatic and alicyclic-substituted aromatic nuclei, and the like, as well as cyclic substituents; substituted hydrocarbon substituents, that is, those substituents containing non-hydrocarbon radicals which do not alter the predominantly hydrocarbon substituent (e.g., halo (especially chloro and fluoro), alkoxy, mercapto, alkylmercapto, nitro, nitroso, sulfoxy, and the like); and hetero substituents, that is, substituents which, while having predominantly hydrocarbyl character, contain other than carbon atoms. Suitable heteroatoms include, for example, sulfur, oxygen, nitrogen, and such substituents as pyridyl, furanyl, thiophenyl, imidazolyl, and the like. Heteroatoms, and typically no more than one, can be present for each carbon atom in the hydrocarbon-based substituents. Alternatively, there can be no such radicals or heteroatoms in the hydrocarbon-based substituent and, therefore, the substituent can be purely hydrocarbon.

Candidate agents of interest also include peptides and derivatives thereof, e.g. high affinity peptides or peptidomimetic substrates for the polypeptide of interest. Generally, peptide agents encompassed by the methods provided herein range in size from about 3 amino acids to about 100 amino acids, with peptides ranging from about 3 to about 25 being typical and with from about 3 to about 12 being more typical. Peptide agents can be synthesized by standard chemical methods known in the art (see, e.g., Hunkapiller et al., *Nature* 310:105-11, 1984; Stewart and Young, *Solid Phase Peptide Synthesis*, $2^{nd}$ Ed., Pierce Chemical Co., Rockford, Ill., (1984)), such as, for example, an automated peptide synthesizer. In addition, such peptides can be produced by translation from a vector having a nucleic acid sequence encoding the peptide using methods known in the art (see, e.g., Sambrook et al., *Molecular Cloning, A Laboratory Manual*, 3rd ed., Cold Spring Harbor Publish., Cold Spring Harbor, N.Y. (2001); Ausubel et al., *Current Protocols in Molecular Biology*, 4th ed., John Wiley and Sons, New York (1999); which are incorporated by reference herein).

Peptide libraries can be constructed from natural or synthetic amino acids. For example, a population of synthetic peptides representing all possible amino acid sequences of length N (where N is a positive integer), or a subset of all possible sequences, can comprise the peptide library. Such peptides can be synthesized by standard chemical methods known in the art (see, e.g., Hunkapiller et al., *Nature* 310:105-11, 1984; Stewart and Young, *Solid Phase Peptide Synthesis*, $2^{nd}$ Ed., Pierce Chemical Co., Rockford, Ill., (1984)), such as, for example, an automated peptide synthesizer. Nonclassical amino acids or chemical amino acid analogs can be used in substitution of or in addition into the classical amino acids. Non-classical amino acids include but are not limited to the D-isomers of the common amino acids, α-amino isobutyric acid, 4-aminobutyric acid, 2-amino butyric acid, γ-amino butyric acid, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

Active compounds can be incorporated into a variety of formulations for therapeutic administration. In general a formulation will comprise an effective dose of the agent, where an effective dose in the concentration of the agent that is sufficient to alter the conformation of conformationally defective proteins during synthesis of the protein, when administered to a target cell or tissue. In some embodiments, an effective dose is sufficient to rescue expression of the conformationally defective protein, such that protein is expressed on the cell surface. The expression may be about 5%, about 10%, about 20% about 30% or more of the surface expression of the wild-type protein, e.g. CFTR.

More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like. Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene. glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres; slabs, etc. with biodegradable or non-biodegradable polymers. For example, polymers of lactic acid and/or glycolic acid form an erodible polymer that is well-tolerated by the host. The implant containing the inhibitory compounds may be placed in proximity to the site of a tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to, be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided compounds of the present invention and other cytotoxic agents has the advantages that the required dosages for the individual drugs is lower, and the effect of the different drugs complementary. Depending on the patient and condition being treated and on the administration route, the subject compounds may be administered in dosages of 0.1 μg to 10 mg/kg body weight, per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat maybe ten times the injection dose. Higher doses maybe used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Agents of Interest. A shown herein, isoliquiritigenin (4,2', 4'-trihydroxychalcone) is active in the assays of the invention, and provides for significant and dose-dependent upregulation of CFTR expression. Isoliquiritigenin may be administered for therapeutic purposes. Therapeutic formulations may be administered at doses that achieve a concentration of from 0.1, about 1 to about 100 μM in the relevant tissues. In some embodiments of the invention, isoliquiritigenin or derivatives thereof is administered as a therapeutic agent for the treatment of cystic fibrosis.

In other embodiments, isoliquiritigenin is used as a control agent in screening methods of the invention, where it provides a pharmaceutical positive control for activity. For such purposes, it may be used at a variety of concentrations, e.g. as disclosed in the examples. In other embodiments, isoliquiritigenin finds use as a target compound for determining structure/activity relationships.

Isoliquiritigenin has the structure:

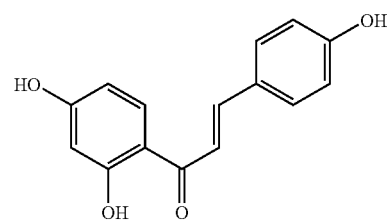

Compounds of interest for screening include those having the generic formula:

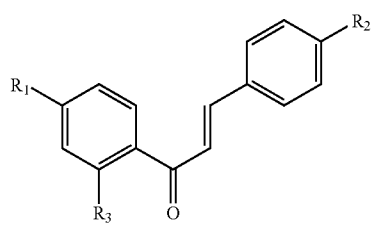

where each of $R_1$, $R_2$, and $R_3$ is individually selected from C, N, O, and S, with H substitution as needed to fulfill open valence sites. Pharmaceutically acceptable esters of at any one or more of the R1 sites may also find use.

In some embodiments, each of $R_1$, $R_2$, and $R_3$ is individually selected from an alkyl, usually branched or linear lower alkyl; hydroxy, alkoxy, aryloxy, haloalkoxy, cyano, nitro, mercapto, alkylthio, —S(O)$_p$R$^6$ (where p is 0 to 2), —S(O)$_p$N(R$^6$)$_2$ (where p is 0 to 2); —OR$^6$, —C(O)OR$^6$, —C(O)N(R$^6$)$_2$, —N(R$^6$)$_2$, —N(R$^6$)C(O)OR$^7$, —N(R$^8$)C(O)R$^8$, and —R$^8$—N═N—O—R$^7$; where each R$^6$, R$^7$ or R$^8$ is independently selected from the group consisting of hydrogen, alkyl, alkenyl, haloalkyl, haloalkenyl, aryl, aralkyl, aralkenyl, cycloalkyl, cycloalkylalkyl and cycloalkylalkenyl.

Derivatives of interest include "pharmaceutically acceptable salts", which include both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)— or (S)— or, as (D) or (L) for amino acids. The present invention is meant to include all such possible isomers, as well as, their racemic and optically pure forms. Optically active (+) and (−), (R)— and (S)—, or (D) and (L) isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Polypeptides of Interest. Polypeptides of interest for the methods of the invention are conformationally defective, in that the polypeptide is not expressed at the cell surface, where the native form of the polypeptide would be expressed at the cell surface. Such polypeptides may be associated with a disease condition. For example, the following table lists human proteins and diseases conditions involving folding and quality control mechanisms, which proteins are of interest for screening by the methods of the invention.

| DISEASE | PROTEIN |
| --- | --- |
| emphysema-liver disease | α1-antitrypsin |
| α1-antichymotrypsin deficiency | α1-antichymotrypsinogen |
| scurvy | procollagen |
| micromelia | Aggrecan |
| osteogenesis imperfecta | procollagens I, II and IV |
| Marfan's syndrome | fibrillin |
| fibrinogen storage disease | fibrinogen |
| Von Willebrand's disease | vW factor |
| diabetes insipidus | vasopressin-vasopressin receptor |
| protein C deficiency | protein C |
| primary hypoparathyroidism | preproparathyroid hormone |
| type I hereditary angioderma | complement C1 |
| factor H deficiency | 155 kDa factor H subunit |
| cystic fibrosis (CF) | cystic fibrosis transmembrane regulator |
| glaucoma | myocilin |
| Glanzmann's thrombasthenia | integrin receptor |
| congenital sucrase-isomaltase deficiency | sucrase-isomaltase |
| hereditary haemochromatosis | transferrin receptor |
| familial hypercholesterolaemia | low-density lipoprotein receptor |
| type I chylomicronaemia | lipoprotein lipase |
| Charcot-Marie-Tooth syndrome | myelin protein 22 |
| Perlizaeus-Merzbacher disease | proteolipoprotein |
| nephrogenic diabetes insipidus (NDI) | aquaporin, vasopressin receptor |
| myeloperoxidase deficiency | myeloperoxidase |
| Laron dwarfism | growth hormone receptor |
| diabetes mellitus | insulin receptor |
| hexosaminidase A deficiency | α-hexosaminidase |
| Sandhoi/Tay-Sachs | β-hexosaminidase |
| Hurler syndrome | α-L-iduronidase |
| aspartylglucoseaminuria | aspartylglucoseaminidase |
| Maroteaux-Lamy syndrome | lysosomal 4-sulphatase |
| GM2-gangliosidosis AB variant | GM2 activator protein |
| Retinitis pigmentosa (RP) | rhodopsin |
| congenital hypothyroid goitre | thyroglobulin |
| abetalipoproteinaemia | microsomal triglyceride transfer protein |
| melanoma | tyrosinase |

AVP, arginine vasopressin; CF, cystic fibrosis; CFTR, CF transmembrane conductance regulator; ERAD, ER-associated degradation; GPCR, G-protein coupled receptor; HTS, high throughput screen; QC, quality control; LQT2, long QT syndrome type 2; NDI: nephrogenic diabetes insipidus; PGP, P-glycoprotein; TM, transmembrane; TMAO: trimethylamine oxide; Ub: ubiqutiin; V2R: vasopressin V2 receptor Among the polypeptides of interest is CFTR, which is a polytopic integral membrane glycoprotein composed of 1,480 amino acids. Over 1,200 mutations and sequence variants in the CFTR gene have been linked to Cystic Fibrosis (CF). These mutations have been grouped into four classes: class I mutations abrogate the synthesis of CFTR protein, class II mutants are defective in protein trafficking, class III mutations lead to the presence of unstable or nonfunctional protein at the plasma membrane, and class IV mutations interfere with channel activation and regulation by physiological agonists. The vast majority of CF patients of Northern European origin have at least one copy of a single mutant allele, ΔF508, which encodes a CFTR molecule lacking a phenylalanine at position 508.

When expressed in cultured epithelial or nonepithelial cells, ΔF508 CFTR is found as an immature, core-glycosylated species localized by immunofluorescence microscopy to the ER membrane, whereas wild-type CFTR is predominantly found as a complex glycosylated species at the plasma membrane. Folding defects in ΔF508 CFTR biosynthesis alter the protein's interactions with the quality control system in the early secretory pathway and also directly or indirectly affect its activity as an anion channel and its stability as a cell surface glycoprotein.

In some embodiments of the invention, the protein of interest is CFTR ΔF508, where the S-tag sequence is inserted in the 4th extracellular loop. Specific sites of interest for insertion include, without limitation, between S895 and T896; between T896 and H897; between H897 and S898; and between S901 and Y902. The insert may comprise one, two, three, four, five or more S-tag sequences, usually two to four S-tag sequences, and may comprise three. The S-tagged protein may be expressed in epithelial cells, including primary epithelial cells, and epithelial cell lines. The S-tagged protein is alternatively expressed in non-epithelial cells.

Among the proteins of interest is myocilin, which is a secreted protein. Myocilin is the trabecular meshwork-induced glucocorticoid response protein (TIGR), mutations in which are associated with open angle glaucoma. A number of mutations in the myocilin gene have been found in glaucoma patients, and are publicly available sequences. It is expressed as a 2.3-kb transcript not only in eye structures but also in heart, skeletal muscle, stomach, thyroid, trachea, bone marrow, thymus, prostate, small intestine, and colon, with lower expression in lung, pancreas, testis, ovary, spinal cord, lymph node, and adrenal gland. The human protein is approximately 58-kD, 504-amino acid, with a leucine zipper domain, 10 putative phosphorylation sites, and 4 potential glycosylation sites. Mutations linked to dominantly inherited glaucoma interfere with secretion of myocilin, causing it to accumulate in the ER as a misfolded protein, ultimately causing cytotoxicity. The mutations associated with disease may interfere with secretion, dimerization, or interaction of TIGR/myocilin with other extracellular matrix components of the trabecular meshwork (see Zhou et al. (1999) Hum. Molec. Genet. 8: 2221-2228, herein incorporated by reference).

In some embodiments of the invention, the protein of interest is myocilin and mutants thereof, P370L and D380A, where the S-tag sequence is inserted after the C-terminal residue (M504). The insert may comprise one, two, three, four, five or more S-tag sequences, usually one S-tag sequence is sufficient for detection. The S-tagged protein may be expressed in retinal cells (e.g. human trabecular meshwork (HTM) cell) or non-retinal cells like HEK293 or CHO cells.

Another protein of interest is arginine vasopressin (AVP), which is a nonapeptide hormone that promotes renal water reabsorption by the kidney, and is associated with nephrogenic diabetes insipidus (NDI). AVP binding to the V2 vasopressin receptor (V2R), a member of the 7 transmembrane G-protein coupled receptor (GPCR) superfamily, initiates a signal transduction cascade leading to the recruitment of aquaporin-2 (AQP2) water channels into the apical membrane of principal cells in the collecting tubule of the kidney, resulting in enhanced water reabsorption. Patients suffering from NDI cannot concentrate their urine, even in the presence of elevated circulating levels of AVP (15). NDI has been linked to loss-of-function mutations in both V2R receptors and AQP2 water channels. More than 155 mutations within the V2R gene have been associated with X-linked NDI, of which about half are missense mutations (16). It has been estimated that more than 90% of the mutants tested lead to the retention and degradation of the mutant V2R receptors in the ER (17) and references therein. Several V2R mutants exhibiting an ER retention phenotypes have been shown to be amenable to rescue by binding to "pharmacological chaperones"—membrane permeant V2R receptor antagonists.

Another protein of interest is rhodopsin, the receptor for light in rod photoreceptors. Rhodopsin is a 7-transmembrane (7-TM) G-proptein coupled receptor that covalently binds the visual pigment 11-cis retinal converting light photons into conformational changes that are transduced into a chemical response in the cytoplasm. Mutations in rhodopsin cause autosomal dominant retinitis pigmentosa (ADRP), a leading cause of adult onset blindness. Many ADRP mutants affect rhodopsin's folding properties and lead to its retention in and degradation from the endoplasmic reticulum. Several rhodopsin mutants exhibiting an ER retention phenotype have been shown to be temperature sensitive and amenable to rescue by binding to analogs of 11-cis retinal, suggesting that ADRP is treatable with pharmacological chaperones.

Methods of Screening Candidate Agents

Samples comprising candidate agent are screened for their effect on folding in an assay with a cell expressing an S-tagged conformationally defective protein. The cell and protein of interest are selected and engineered as previously described.

Cells comprising genetic sequences encoding an S-tagged protein of interest are grown in culture for a period of time sufficient to express the S-tagged protein of interest, in the absence of presence of a candidate agent. The agents are conveniently added in solution, or readily soluble form, to the medium of the cells. The agents may be added in a flow-through system, as a stream, intermittent or continuous, or alternatively, adding a bolus of the compound, singly or incrementally, to an otherwise static solution. Preferred agent formulations do not include additional components, such as preservatives, that may have a significant effect on the overall formulation.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype. Positive controls may include, e.g. the wild-type non-conformationally defective protein; the S-tagged protein under conditions known to stabilize folding, the pharmacological agents shown to be active in the examples of the present disclosure, and the like.

Cells are contacted with a candidate agent or suitable controls for a period of time sufficient for expression, e.g. for at least about 6 hours, at least about 12 hours, at least about 24 hours, at least about 48 hours, at least about 72 hours, or more, usually not more than about 1 week. Following the period of time sufficient for expression, the cells are contacted with extracellular S-protein and a substrate for detection of enzymatic activity. In the presence of agents or conditions that are sufficient to stabilize the S-tagged protein and allow it to reach the cell surface, the RNAse is complemented, and activity is detected by cleavage of the substrate. In some embodiments, the cleavage is detected by a colorimetric or fluorometric change.

The change in substrate cleavage in response to the agent is measured, desirably normalized, and the resulting profile may then be evaluated by comparison to reference profiles. The reference profiles may include readouts in the presence and absence of other agents, e.g. antibiotics with known action, positive controls, etc. Agents of interest for analysis include any biologically active molecule with the potential to modulate translation.

Any compatible substrate surface that is transparent to light can be used in conjunction with this invention. The surface can be any of a variety of organic or inorganic materials or combinations thereof, including, merely by way of example, plastics such as polypropylene or polystyrene; silicon; (fused) silica, quartz or glass. In a preferred embodiment, the surface is the plastic surface of a multiwell plate, e.g., tissue culture dish, for example a 24-, 96-, 256-, 384-, 864- or 1536-well plate. The shape of the surface is not critical. It can, for example, be a flat surface such as a square, rectangle, or circle; a curved surface; and the like. Alternatively, a surface such as a glass surface can be etched out to have, for example, 864 or 1536 discrete, shallow wells. Alternatively, a surface can comprise regions with no separations or wells, for example a flat surface, e.g. piece of plastic or glass with individual regions that are defined by overlaying a structure that delineates the separate regions. In another embodiment, the regions can be defined as tubes or fluid control channels, e.g., designed for flow-through assays, as disclosed, for example, in Beattie et al (1995). *Clin. Chem.* 4:700-706. Tubes can be of any size, e.g., capillaries or wider bore tubes. The relative orientation of the test regions can take any of a variety of forms including, but not limited to, parallel or perpendicular arrays within a square or rectangular or other surface, radially extending arrays within a circular or other surface, or linear arrays, etc.

Each of the assays or procedures described below can be performed in a high throughput manner, in which a large number of samples (e.g., as many as about 864, 1036, 1536, 2025 or more) are assayed on each plate or surface rapidly and concurrently. Further, many plates or surfaces can be processed at one time. For example, in methods of drug discovery, a large number of samples, each comprising a drug candidate (e.g., a member of a combinatorial chemistry library, such as variants of small molecules, peptides, oligonucleotides, or other substances), can be added to separate wells; and assays can be performed on each of the samples. With the recent advent and continuing development of high-density microplates, robotics, improved dispensers, sophisticated detection systems and data-management software, the methods of this invention can be used to screen or analyze thousands or tens of thousands or more of compounds per day.

Optionally, candidate agents having activity in the assays of the invention are rescreened by a different assay, where the agent is combined with cells expressing the polypeptide of interest, which is optionally the S-tagged form of the polypeptide; and the rescue of expression determined by antibody staining, e.g. at the cell surface, immunoprecipitation, and the like.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

This invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "and", and "the" include plural referents unless the context clearly dictates otherwise. Thus, for example, reference to "a specific binding pair" includes a plurality of such specific binding pairs and reference to "the complementing domain" includes reference to one or more complementing domains and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed. All publications mentioned herein are incorporated herein by reference to disclose and describe the methods and/or materials in connection with which the publications are cited.

EXPERIMENTAL

Example 1

Cell-based screen for high copy suppressors of ΔF508 misfolding. A genetic screen in mammalian cells was designed to identify critical genes whose functions could promote correct folding and cell surface expression of ΔF508-CFTR protein. The underlying assumption is that either direct overexpression of a protein that facilitates ΔF508-CFTR folding, or expression of a gene fragment that decreases expression or interferes with the function of genes that impede maturation of ΔF508-CFTR, will result in the elevated expression of the ΔF508-CFTR protein at the cell surface.

A fusion protein of green fluorescent protein (GFP) and ΔF508-CFTR was generated, containing a FLAG epitope in the $4_{th}$ extracellular loop. CFTR-FLAG has been characterized before and was found to be very similar to CFTR in terms of its functional, biochemical properties and intracellular processing. It was verified that the intracellular processing and turnover of the GFP-ΔF508-CFTR fusion protein is similar to ΔF508-CFTR. The GFP-ΔF508-CFTRFLAG construct was stably introduced into CHO/EcoR cells (a CHO subline expressing an ecotropic retroviral receptor). Background expression of ΔF508-CFTR-FLAG on the cell surface of these cells is negligible at physiological temperature; therefore an increase in anti-FLAG reactivity in intact cells should be due delivery to or stabilization of ΔF508-CFTR-FLAG at the cell surface. GFP fluorescence allows us to monitor total expression of GFP-ΔF508-CFTR, and deployment of GFP-ΔF508-CFTR-FLAG to the plasma membrane is expected to be accompanied by stabilization of the protein and a consequent increase in the GFP fluorescence. Thus, cells with highest fluorescence in both GFP and anti-FLAG channels can be detected by FACS. ΔF508-CFTR has a temperature sensitive phenotype and a small but significant fraction of ΔF508-CFTR molecules can fold and reach the cell surface when cells are cultured at reduced temperature or in the presence of "chemical chaperones" such as glycerol.

Screening procedure: A human lung cDNA library in the high-titer retroviral pFBXR vector was transduced into CHO/EcoR/GFP-ΔF508-CFTR-FLAG. 48 h after transduction, live cells were harvested, stained, without permeabilization, with anti-FLAG antibody and secondary fluorescent antibody and the most fluorescent 1-3% of cells were sorted by FACS. Sorted cells were expanded in culture for approximately 10 days and staining and the sorting procedure was repeated twice more. After three rounds of selection genomic DNA was isolated from sorted cells, inserts were amplified by PCR with vector-specific primers, cloned into TOPO vector and sequenced. Unfortunately, this screen did not yield any consistently positive clones.

Example 2

No high affinity ligands or chemical chaperones have previously been identified for ΔF508-CFTR. An RNAase S assay is used to screen for facilitators of ΔF508-CFTR surface expression.

Generation of reporters bearing cell surface displayed S-tags. Wild-type and ΔF508 CFTR were prepared with an S-tag sequence introduced into various positions, as shown in Table 1. PCR mutagenesis was used to introduce a linker containing Nhe I (5') and SacII (3') restriction sites into human CFTR cDNA at four different insertions points, designated A-D. To insert S-tags, the recominant plasmids were digested with NheI and SacI and ligated together with double stranded oligonucleotides encoding S-tags and glycine-rich flanking sequences. Double tandem S-tag insertions were constructed by ligating oligonucleotides encoding double S-tag sequences. Longer S-tag repeats were constructed by annealing single and double S-tag encoding oligonucleotides together and screening for restriction fragments of the expected size.

Figure 2:
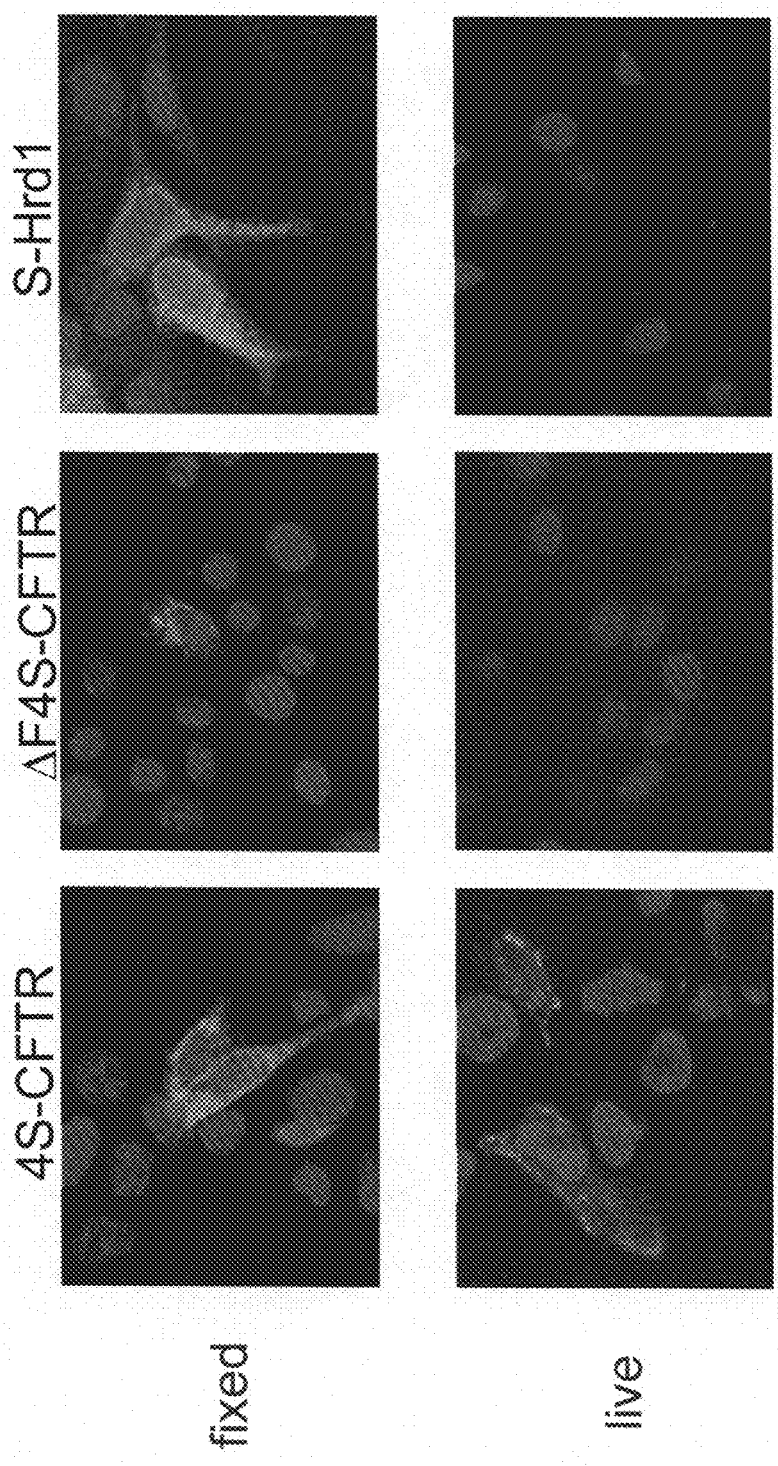
FIG. 2. Cell surface accessibility of S-tag in 4S-CFTR and 4S-CFTRΔF508. HEK 293 cells transiently transfected with the indicated constructs were subjected to indirect immunofluorescence labeling with antibody to S-tag (green) in fixed and permeabilized (upper panels) or live (lower panels) cells. HRD1-S is an S-tagged ER-resident protein. DNA is stained with bisbenzimide (blue).

These constructs were expressed by transient transfection into HEK-293 cells and analyzed initially by screening cell lysates via western blot using (1) antibodies against the CFTR C-terminus to test for complete open reading frame (designated "C") (2) antibodies against the S-tag to test for the presence of the S-tag (designated "T") and (3) S-protein HRP to test for the accessibility of the S-tag to S-protein. Only two constructs, containing 3 or 4 S-tages at insertion site "A" scored positive by all three assays. These were further analyzed by fluorescence microscopy of permeabilized or intact cells using antibody to S-tag (FIG. 2). A positive control for this experiment was to express a mutant form of CD4 (FIG. 1) that had been tagged recombinantly with S-peptide at its N-terminus (The CD4 construct is a mutant lacking the entire cytoplasmic domain so that it does not signal. The S-tag was inserted immediately following the signal peptide by standard mutagenesis).

Figure 3:
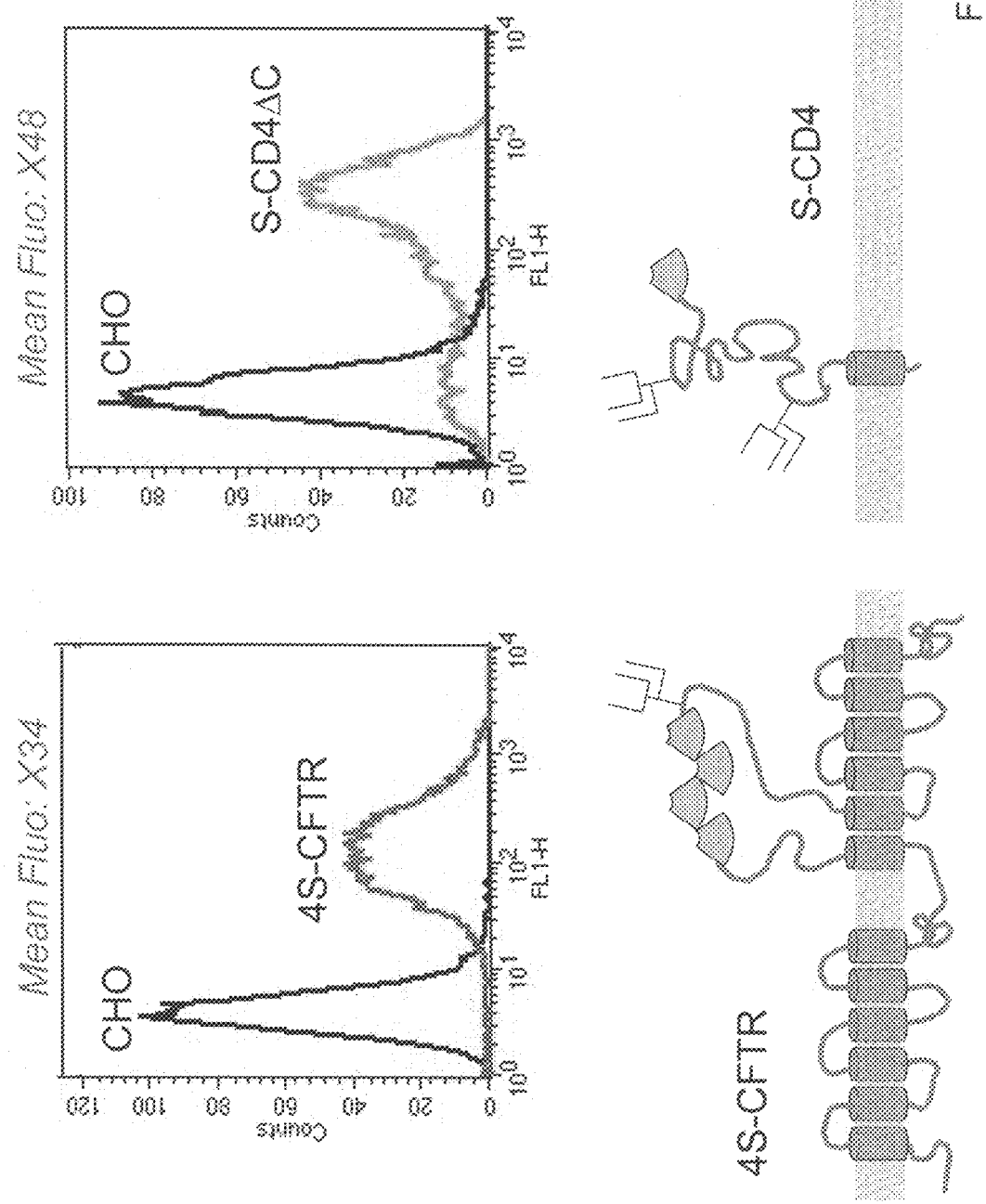
FIG. 3. Detection of S-tagged CFTR and CD4 by flow cytometry. Fluorescence histograms showing anti-S-tag antibody binding to cell surface in live, unfixed CHO cells untransfected or stably expressing the indicated S-tagged constructs.
Figure 4:
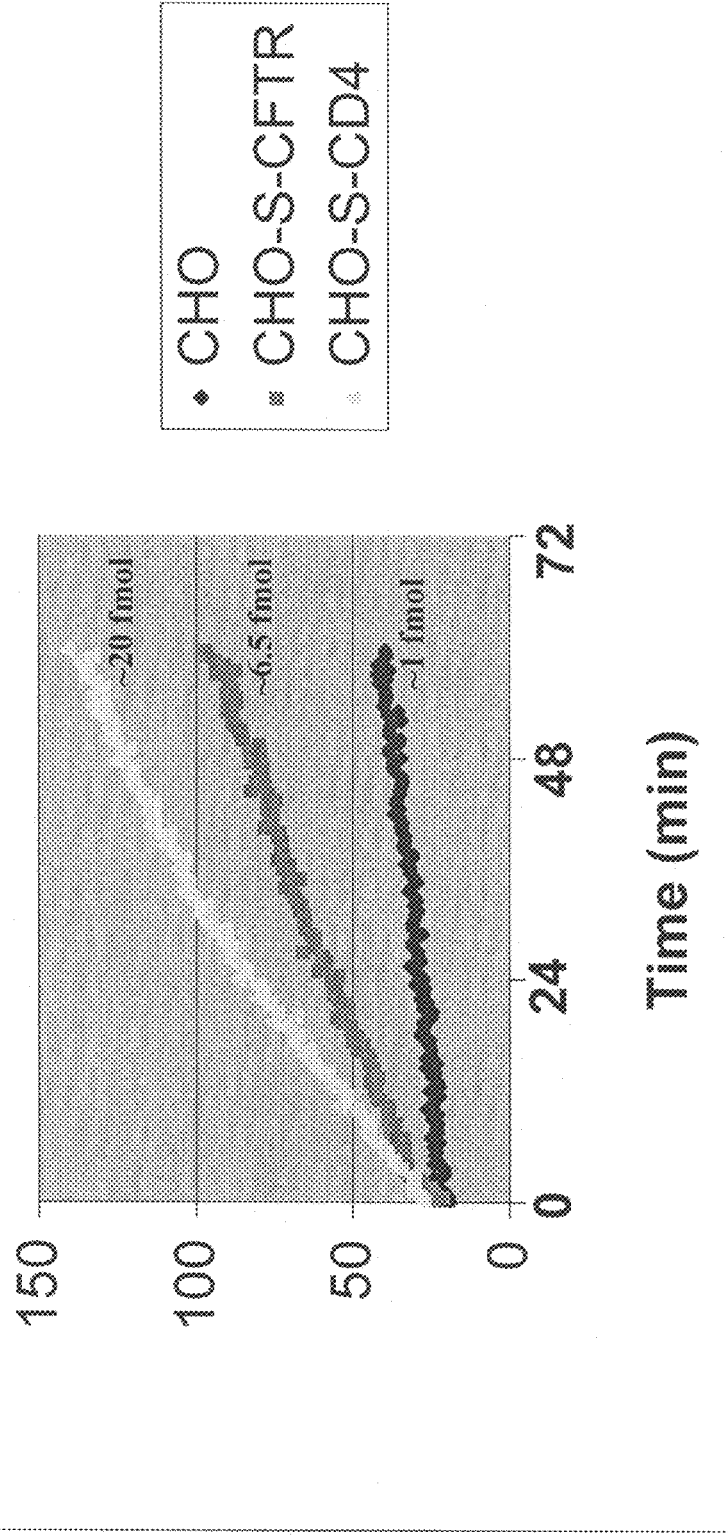
FIG. 4. Time course of RNAase activity in cell lines from FIG. 7. Numbers indicate calculated level of S-peptide present on the cell surface determined by comparison with calibration curve as in FIG. 3.

The extent of cell surface S-tag expression for both constructs was quantified in live cells by flow cytometry (FIG. 3). To evaluate the utility of the RNAase based assay for detection of S-tagged membrane proteins in live cells, stable CHO cell lines expressing these contstructs were established and selected for high surface expression by FACS. These lines were tested for cell surface RNAase activity by the addition of S-protein and substrate as described below (FIG. 4).

Figure 5:
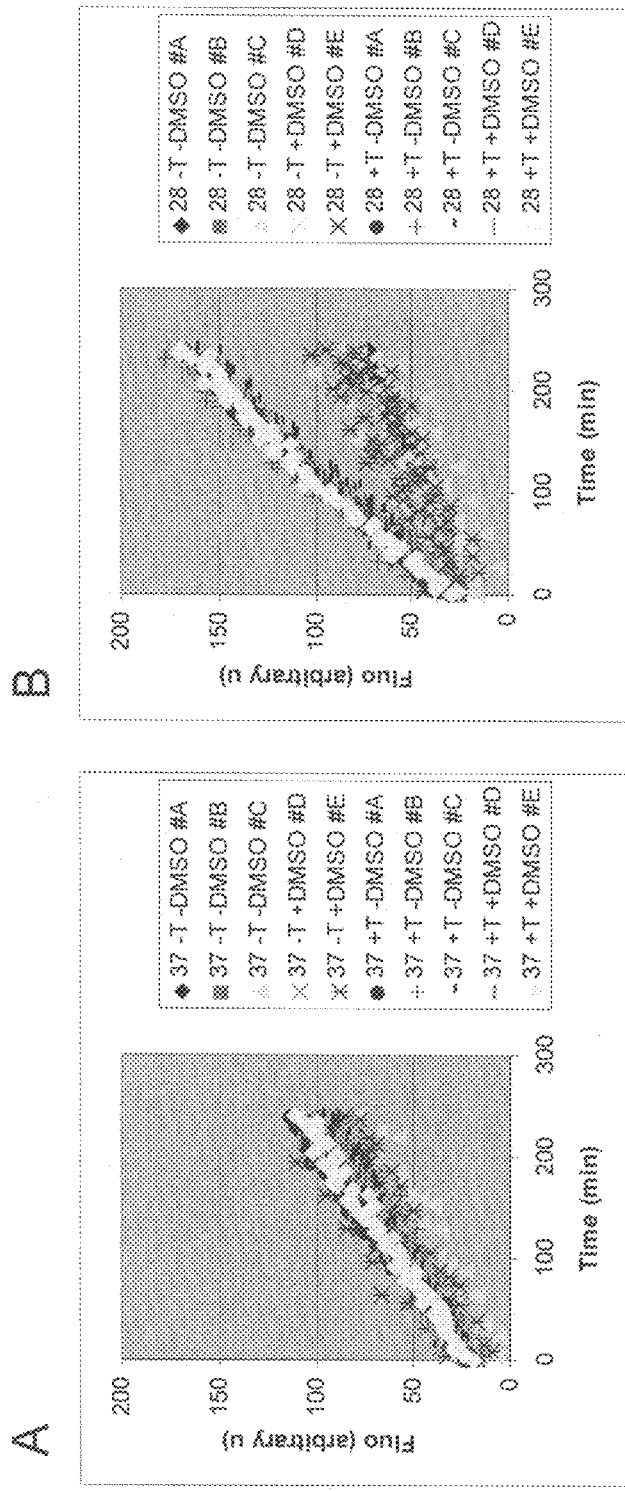
FIG. 5A-5B. Rescue of 4S-CFTRΔF508 by low temperature detected by RNAase assay. (A). RNAase activity in 4S-CFTRΔF508 expressing CHO cells cultured at 37° for 48 hrs in the presence or absence of tetracycline. (B) RNAase activity in 4S-CFTRΔF508 expressing CHO cells cultured at 28° for 48 hrs in the presence or absence of tetracycline. Data are mean±SD for 5 independent experiments. Tet-inducible clonal 4S-CFTRΔF508 expressing cells were plated in 96 well dishes and cultured as indicated for 48 hrs. For RNAase assay the well were washed 3× in HBSS and assayed by the addition of 10 nM substrate and 2.5 pmol S-protein in a total volume of 200 µl at room temperature for the times indicated.
Figure 6:
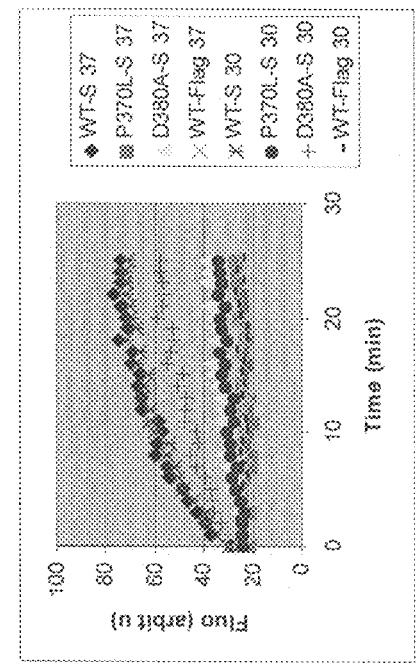
FIG. 6A-6B. Rescue of mutant myocilin secretion by low temperature. (A) Immunoblot analysis of media from cells expressing wildtype myocilin tagged with S-peptide and two glaucoma mutants grown at 37° or 30°. Effect of low temperature quantified by densitometry, is shown in lower panel. (B) Rescue of myocilin mutants by low temperature growth assayed by RNAase activity secreted into culture media.
Figure 6:
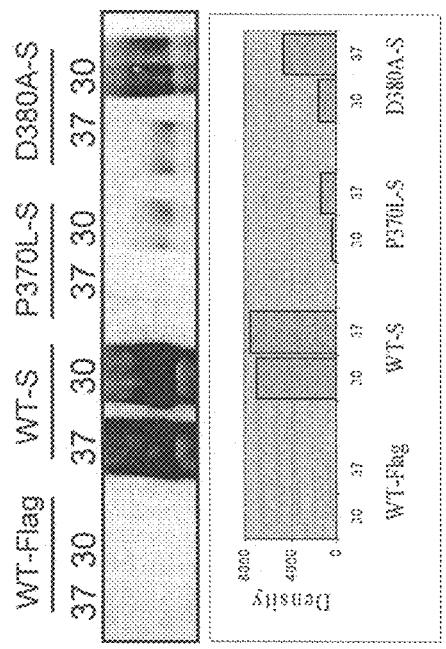

To assess the ability to detect rescue of DF508 CFTR by low temperature incubation, a clonal line of CHO cells was established in which 4S-DF508 CFTR expression is regulated by a tetracycline-inducible promoter (constitutive expression of DF508 CFTR is toxic to cells). Cell surface RNAase activity in tetracycline induced or uninduced cells cultured for 48 hr at 37° was not significantly different from that observed in untransfected CHO cells (FIG. 5A). Similarly low background RNAase activity was observed in 4S-DF508 CFTR expressing CHO cells cultured at 28° in the absence of inducer (FIG. 5B). Notably, significant elevation in RNAase activity was detected in cells cultured in the presence of inducer at 28° (5B).

```
CFTR constructs with S-tag in the 4th extracellular loop  [SEQ ID NO:15]
(-L W L L G N T P L Q D K G N S T H S R N N S Y A V I I T S T S)
881                          894 A B C       900 D           911
```

| | | C | T | S |
|---|---|---|---|---|
| Site A: between S895 and T896 | | | | |
| S{AS[GGGG(KETAAAKFERQHMDS)GGGG]TR}T | [SEQ ID NO:16] | + | + | − |
| S{AS[GGGG(KETAAAKFERQHMDS)GGGG(KETAAAKFERQHMDS)GGGG]TR}T | [SEQ ID NO:17] | + | + | ± |
| S{AS[GGGG(KETAAAKFERQHMDS)GGGG(KETAAAKFERQHMDS)GGGG]PR}T | [SEQ ID NO:18] | + | + | ± |
| S{AS[GGGG(KETAAAKFERQHMDS)GGGG(KETAAAKFERQHMDS)GGGG(KETAAAKFERQHMDS)GGGG]PR}T | [SEQ ID NO:19] | + | + | + |
| S{AS[GGGG(KETAAAKFERQHMDS)GGGG(KETAAAKFERQHMDS)GGGG(KETAAAKFERQHMDS)GGGG(KETAAAKFERQHMDS)GGGG]PR}T | [SEQ ID NO:20] | + | + | + |
| S{AS[SG(KETAAAKFERQHMDS)PPPSG]TR}T | [SEQ ID NO:21] | + | + | − |
| S{AS[SG(KETAAAKFERQHMDS)PPPSGL-COOH | [SEQ ID NO:22] | − | + | + |
| S{AS[GM(KETAAAKFERQHMDS)PDLG]TR}T | [SEQ ID NO:23] | + | + | − |
| Site B: between T896 and H897 | | | | |
| T{LQ[DD(KETAAAKFERQHMDS)DD]PG}H | [SEQ ID NO:24] | + | + | − |
| T{LH[GDD(KETAAAKFERQHMDS)DDG]SG}H | [SEQ ID NO:25] | + | + | − |

-continued

```
CFTR constructs with S-tag in the 4th extracellular loop    [SEQ ID NO:15]
(-L W L L G N T P L Q D K G N S T H S R N N S Y A V I I T S T S)
881                       894 A B C       900 D           911
```

|  | | C | T | S |
|---|---|---|---|---|
| T{LH[GDD(KETAAAKFERQHMDS)GDDG(KETAAAKFERQHMDS)DDG]SG}H | [SEQ ID NO:26] | + | + | − |
| T{AS[GGGG(KETAAAKFERQHMDS)GGGG(KETAAAKFERQHMDS)GGGG(KETA AAKFERQHMDS)GGGG]PR}H | [SEQ ID NO:27] | + | + | − |
| T{LH[GDD(KETAAAKFERQHMDS)GDDG(KETAAAKFERQHMDS)GDDEKKQQQQ NLKDNTWIAMMDPGIVEITAMQ-COOH | [SEQ ID NO:28] | − | + | ± |
| T{LH[GD(KETAWAKFEDQHMDS)G(KETAWAKFEDQHMDS)DG]SG}H | [SEQ ID NO:29] | + | − | − |
| T{LH[GD(KETAWAKFEDQHMDS)G(KETAWAKFEDQHMDS)G(KETAWAKFEDQH MDS)DG]SG}H | [SEQ ID NO:30] | + | − | − |
| T{LH[GD(KETAWAKFEDQHMDS)DG]SG}H | [SEQ ID NO:31] | + | − | − |
| T{LH[GD(KETAWAEFERQHMDS)G(KETAWAEFERQHMDS)DG]SG}H | [SEQ ID NO:32] | + | − | − |
| T{LH[GD(KETAWAEFEDQHMDS)G(KETAWAEFEDQHMDS)DG]SG}H | [SEQ ID NO:33] | + | − | − |

Site C: between H897 and S898

| H{SLE(KETAAAKFERQHMDS)A}S | [SEQ ID NO:34] | + | + | − |
| H{AS[GGGG(KETAAAKFERQHMDS)GGGG]TR}S | [SEQ ID NO:35] | + | + | − |
| H{AS[GGGG(KETAAAKFERQHMDS)GGGG(KETAAAKFERQHMDS)GGGG(KETA AAKFERQHMDS)GGGG]PR}S | [SEQ ID NO:36] | + | + | − |
| H{AS[SG(KETAAAKFERQHMDS)PPPSG]TR}S | [SEQ ID NO:37] | + | + | − |
| H{AS[SG(KETAAAKFERQHMDS)PPPSGL-COOH | [SEQ ID NO:38] | − | + | ± |
| H{AS[GM(KETAAAKFERQHMDS)PDLG]TR}S | [SEQ ID NO:39] | + | + | − |

Site D: between S901 and Y902

| S{(KETAAAKFERQHMDS)}Y | [SEQ ID NO:40] | + | + | − |
| S{AS[GGGG(KETAAAKFERQHMDS)GGGG(KETAAAKFERQHMDS)GGGG(KETA AAKFERQHMDS)GGGG]PR}Y | [SEQ ID NO:41] | + | + | − |

C: anti-CFTR antibody; T: anti-s-tag antibody; S: s-protein-HRP
Bold-type residues are mutants with reported higher affinity.
N894 and N900 are sites of N-glycosylation Assess intracellular localization, folding and trafficking of reporters. The stable lines expressing S-tagged wild-type, and ΔF508-CFTR were evaluated for the following parameters both under naïve conditions and following incubation at reduced temperature (26° C. for 48 hr).

Optimize conditions for homogeneous cell-based assay for ΔF508-CFTR rescue. Surface detection of S-protein tagged CFTR used reconstitution of RNAase S activity and detection with the fluorogenic probe 6-F-dArUdAdA-6-TMR.

Screening was carried out on a customized apparatus (SAGIAN, Beckman) containing a 3-m rail Optimized Robot for Chemical Analysis that integrates the following robot-accessible instruments on a 4×2-m optical table: (a) SAGIAN 180 $CO_2$ incubator, which holds 180 standard microplates in a storage carousel; (b) Elx405-Select plate washer with valve option and vacuum-sensing/waste alert for complex automated wash cycles; (c) SAGIAN MPS-8 CS incubator (holds eight standard microplates at 4-37±1° C.); (a) SAGIAN shaker (six plate positions, frequency range 40-1100 rpm with variable amplitude); (e) Biomek 2000 liquid handling work station (installed with four positions to hold tip boxes with automatic air locks and six positions for microplates and liquid reservoirs, and MP 20 and MP 200 8-channel tip tools for liquid transfer); (f) SAGIAN carousel (holding 40 pipette tip boxes and 90 microplates); (g) SAGIAN bar code reader; (h) SAGIAN microplate lidding station with automatic vacuum control of six suction cups; (i) two FluoStar fluorescence plate readers (BMG Lab Technologies), each equipped with two-syringe pumps.

Data collection and analysis. HeLa or CHO cells stably expressing ΔF508-CFTR were plated at 50,000 per well on 96 well microtiter plates containing individual test compounds at a final concentration of 10 μM. Baseline measurements were obtained following addition of the fluorogenic FRET RNAase substrate 6-F-dArUdAdA-6-TMR, and fluorescence at 520 nm was monitored in individual wells at timed intervals following addition of the complementing S-protein. Control studies were performed with CFTR-S-peptide to determine maximal signal strength, subsequently with ΔF508-CFTR-S incubated at 26° C. to rescue mutant protein to the cell surface. These samples as well as controls expressing similar levels of the same mutant and wild-type membrane proteins lacking S-tag may be routinely included in each high-throughput screening experiment. Additionally wells containing known amounts of purified recombinant RNAase S and free S-peptide may used to calibrate the assay. Positive hits are subjected to a second round of screening under similar conditions to ensure reproducibility. Full dose-response curves are determined on all compounds that survive this replication.

Example 3

Myocilin and mutants thereof, P370L and D380A were S-tagged, where the S-tag sequence was inserted after the C-terminal residue (M504). The S-tagged protein was expressed by transient transfection in HEK-293 cells. The cells were grown at 37 for 48 hrs then transferred into serum-free media and further cultured for 24 hrs at 30° or 37°. Culture media was collected and analyzed by western blotting using myocilin antibody (10-20 μl FIG. 11A) or by RNAase analysis (FIG. 11B). For RNAase analysis, 8 μl of culture medium was added to 200 μl reaction containing 10 nM substrate and 2.5 pmol S-protein in Hank's balanced salt solution (HBSS) (this is the same condition used in the assay in ex. 2).

We have tagged myocilin with S-tag and have used the enzymatic recombination assay to detect it in media. The data indicate that the assay can detect secreted myocilin in less than 1 µl of media; we use this assay to observe rescue by low temperature incubation.

Example 4

Library screening. The LOPAC1280 (Library of Pharmacologically Active Compounds, Sigma Aldrich) compound library contains 1,280 pharmacologically active Sigma-RBI compounds arrayed in 96-well format. Each compound is supplied as 250 µl at 10 mM in DMSO (dimethylsulfoxide). Each compound in the primary screen was tested at several concentrations.

Figure 7:
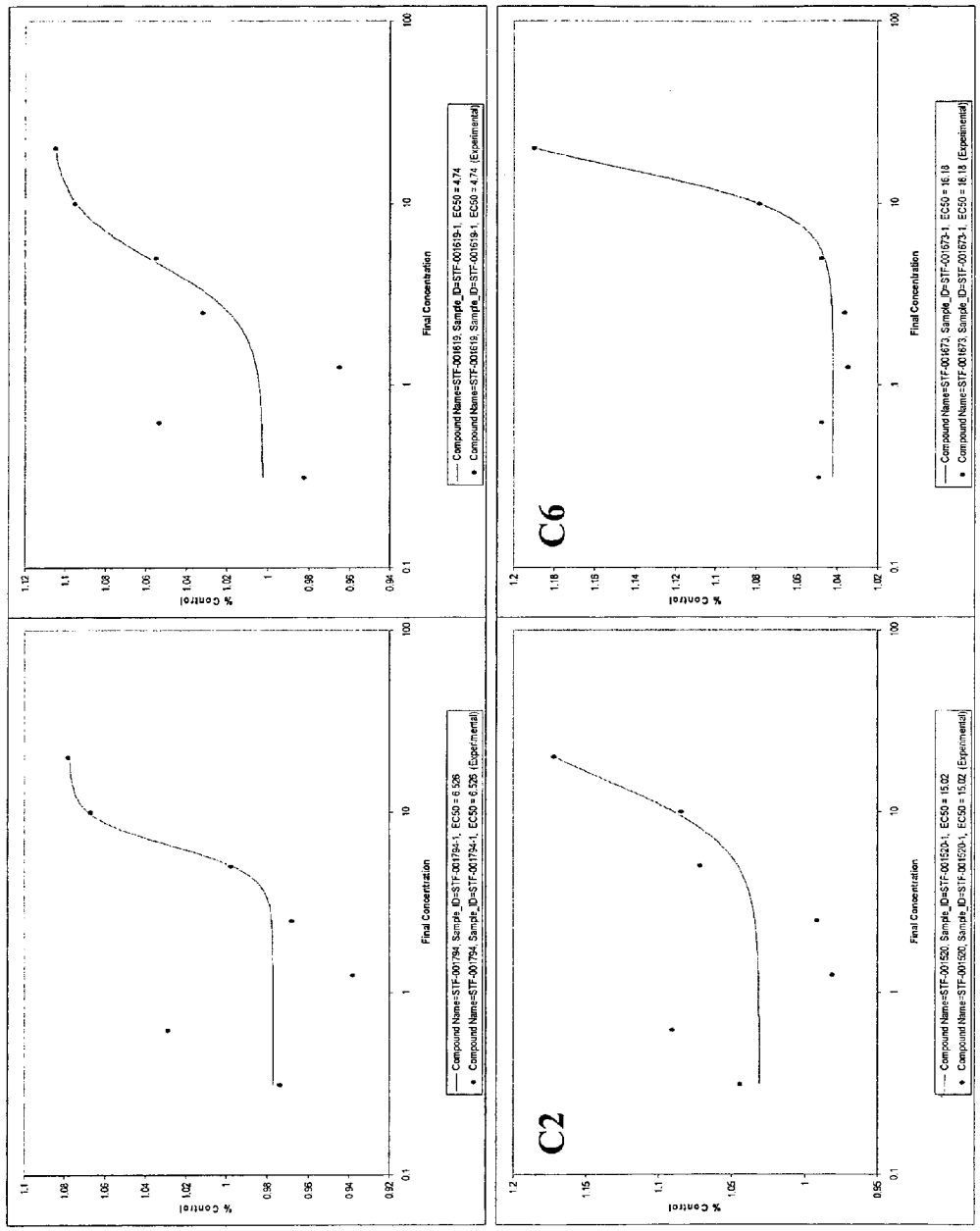
FIG. 7. Results of RNAase assay against 4 candidate compounds selected from a library, screened against 4S-ΔF508 CFTR expressing cells.
Figure 8:
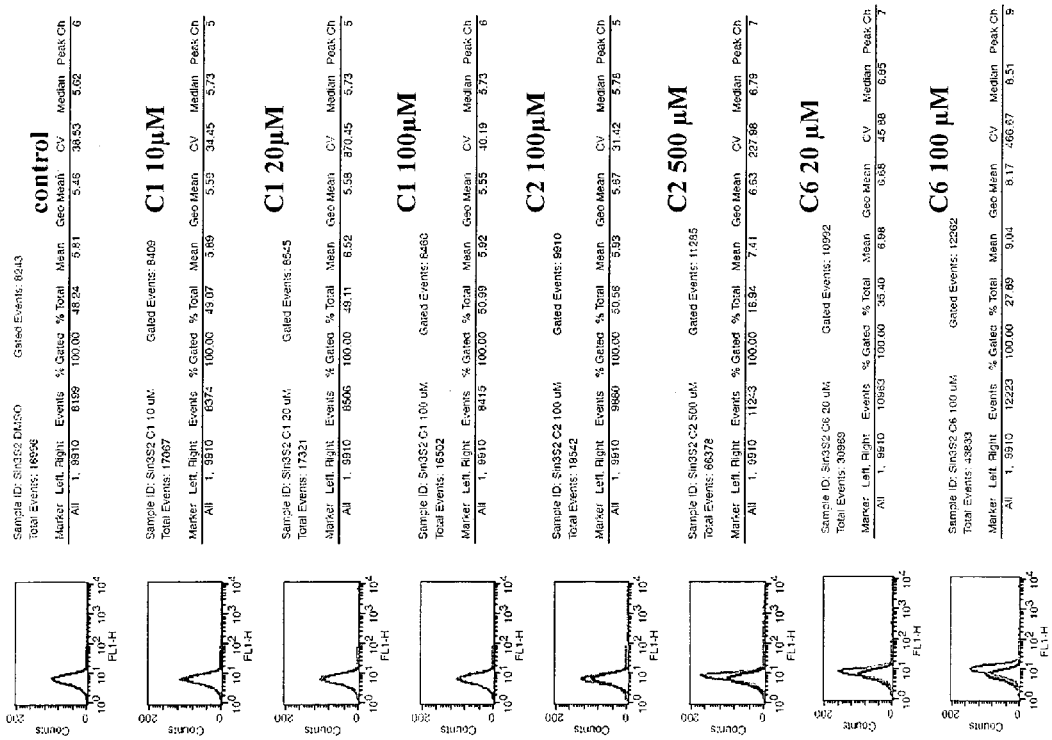
FIG. 8. Rescreening of candidate compounds in a FACS assay to measure S-tag epitopes at the cell surface with a polyclonal antibody.

The library was screened against 4S-ΔF508 CFTR expressing CHO cells using the assay described in Example 2 above. The data from this assay with the 4 best compounds is shown in FIG. 7. Each of these compounds was retested using an FACS assay to measure S-tag epitopes at the cell surface with a polyclonal antibody, as shown in FIG. 8.

Figure 9:
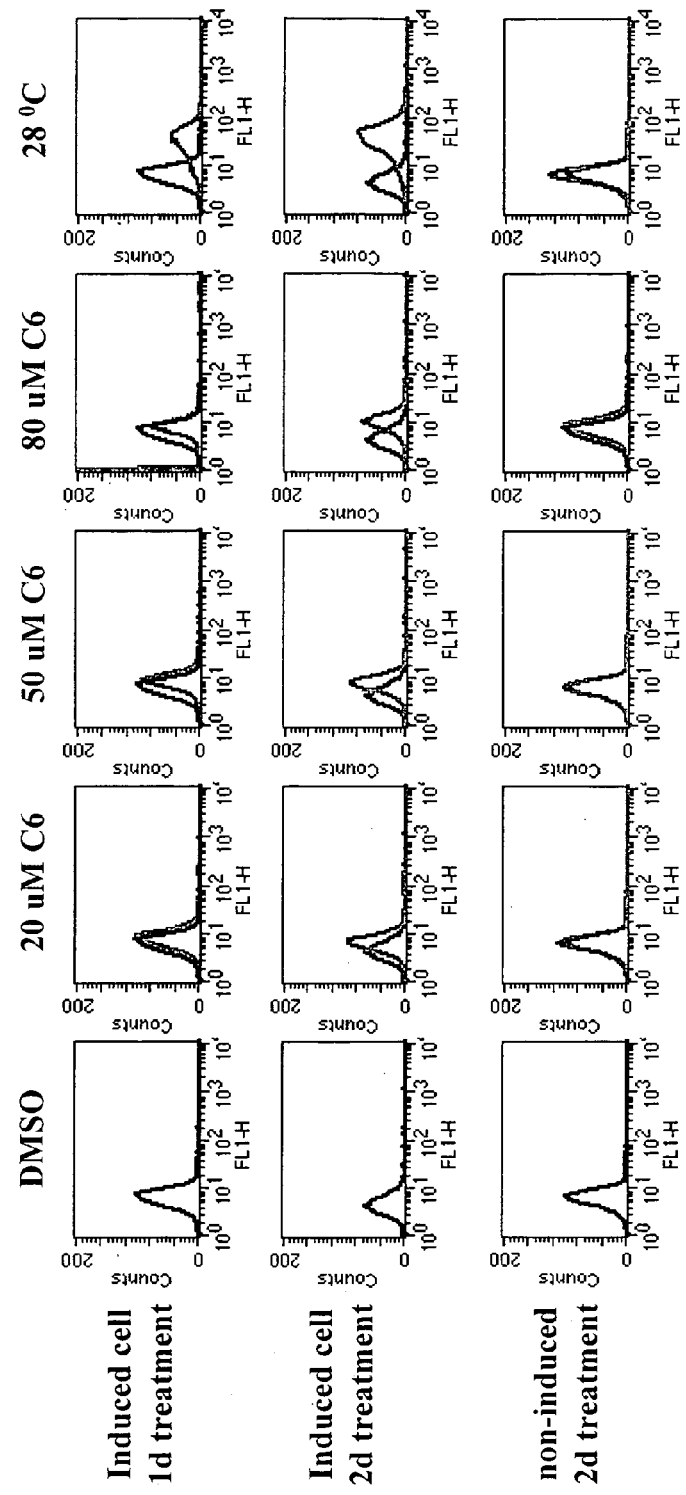
FIG. 9. FACS analysis shows that administration of compound 6, isoliquiritigenin (4,2',4'-trihydroxychalcone), provides for significant, dose dependent increase in surface expression of CFTR.
Figure 10:
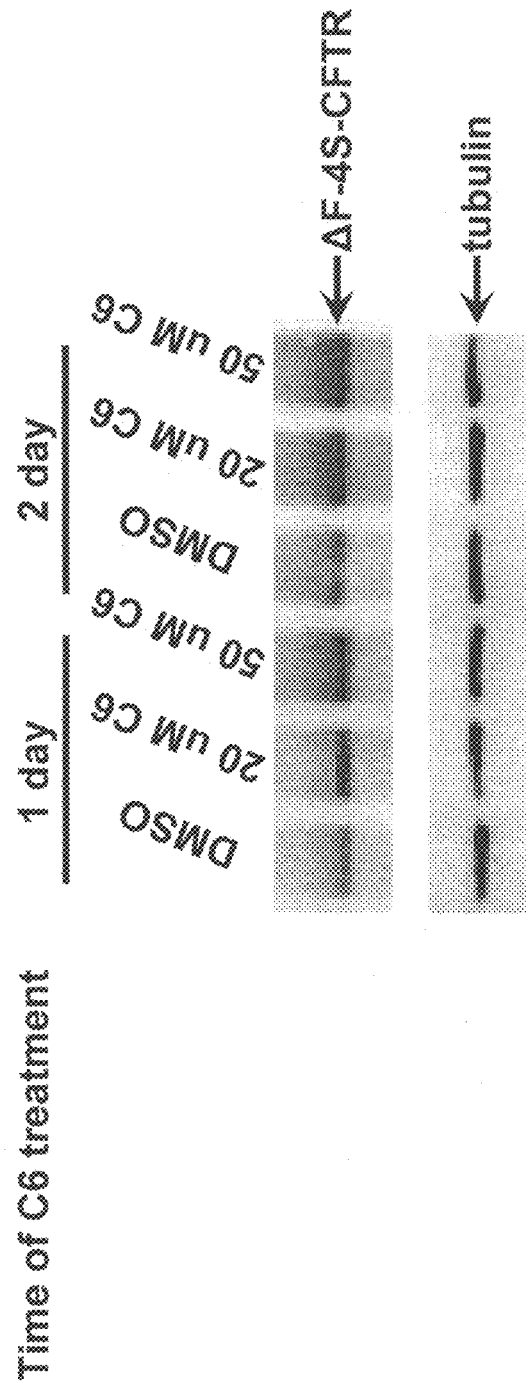
FIG. 10 is a western blot showing the effect of compound 6 on CFTR expression.
Figure 11:
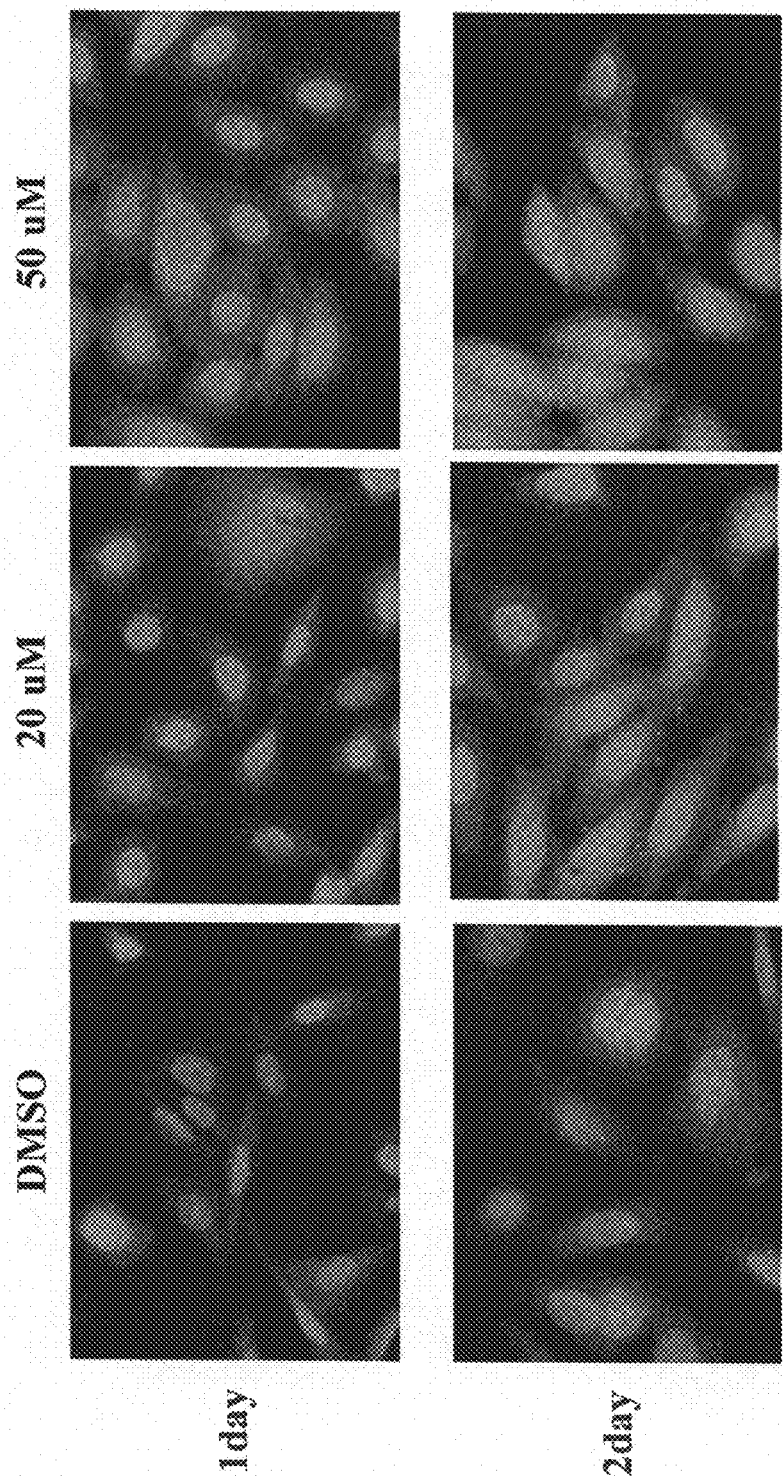
FIG. 11 shows immunofluorescence labeling using polyclonal S-tag antibody on cells exposed to compound 6 at varying doses.

Compound 6 (Isoliquiritigenin (4,2',4'-trihydroxychalcone) was shown to be active in the rescreening assays. This assay was repeated and expanded for cells exposed to different concentrations of compound 6 for 1 or 2 days with or without induction of 4S tag delta F508 expression, and was compared with cells incubated at 28° C. (a positive control). It is evident that a significant, dose dependent increase in surface expression is seen with compound 6 (FIG. 9). The increased expression is also reflected by the increased expression of the protein assessed by western blotting (FIG. 10) and by immunofluorescence labeling using polyclonal S-tag antibody (FIG. 11).

These data demonstrate the efficacy of the screening method of the invention for the identification and classification of agents with chaperone activity, particularly the identification and classification of small molecule chemical and pharmacological chaperones. The agents thus identified find use altering the conformation of otherwise conformationally defective proteins.

What is claimed is:

1. A method of screening a candidate agent for chaperone activity, the method comprising:
   combining a candidate biologically active agent with a cell comprising genetic sequences encoding an S-tagged conformationally defective protein of interest wherein said S-tag of said S-tagged conformationally defective protein of interest comprises at least three S-tag sequences;
   culturing said cell under conditions wherein said S-tagged conformationally defective protein of interest is expressed;
   contacting said cells with S-protein and an RNAse cleavage substrate;
   detecting cleavage of said substrate; and
   determining the chaperone activity of said candidate biologically active agent, wherein an agent that alters folding of said protein results in increased secretion or expression of said protein on the cell surface and increased cleavage of said substrate.

2. The method according to claim 1, wherein said S-tag is introduced between S895 and T896 of ΔF508-cystic fibrosis transmembrane conductance regulator (CFTR).

3. A method of screening a candidate agent for chaperone activity, the method comprising:
   combining a candidate biologically active agent with a cell comprising genetic sequences encoding an S-tagged conformationally defective protein of interest, wherein said S-tag comprises three S-tag sequences;
   culturing said cell under conditions wherein said S-tagged conformationally defective protein of interest is expressed;
   contacting said cells with S-protein and an RNAse cleavage substrate;
   detecting cleavage of said substrate;
   determining the chaperone activity of said candidate biologically active agent, wherein an agent that alters folding of said protein results in increased secretion or expression of said protein on the cell surface and increased cleavage of said substrate.

4. The method according to claim 3, wherein said conformationally defective protein of interest is a human protein.

5. The method according to claim 4, wherein said conformationally defective protein of interest is a conformationally defective mutant of cystic fibrosis transmembrane conductance regulator (CFTR).

6. The method according to claim 5, wherein said conformationally defective protein of interest is ΔF508-CFTR.

7. The method according to claim 6, wherein said S-tag is introduced into the $4^{th}$ extracellular loop of said ΔF508-CFTR.

* * * * *